US009364468B2

(12) United States Patent
Kim et al.

(10) Patent No.: US 9,364,468 B2
(45) Date of Patent: Jun. 14, 2016

(54) PHARMACEUTICAL COMPOSITION FOR PREVENTING OR TREATING TUBERCULOSIS

(71) Applicant: INDUSTRY-ACADEMIC COOPERATION FOUNDATION, YONSEI UNIVERSITY, Seoul (KR)

(72) Inventors: Young Min Kim, Seoul (KR); Seung Jung Han, Seoul (KR); Tae Gwon Oh, Seoul (KR); Sae Woong Park, Seoul (KR); Sang Nae Cho, Seoul (KR); Mi Young Hahn, Seoul (KR); Jee Hee Suh, Daejeon (KR); Kyu Yang Yi, Daejeon (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/382,548

(22) PCT Filed: Feb. 13, 2013

(86) PCT No.: PCT/KR2013/001122
§ 371 (c)(1),
(2) Date: Sep. 2, 2014

(87) PCT Pub. No.: WO2013/137563
PCT Pub. Date: Sep. 19, 2013

(65) Prior Publication Data
US 2015/0133503 A1 May 14, 2015

(30) Foreign Application Priority Data

Mar. 13, 2012 (KR) ........................ 10-2012-0025449

(51) Int. Cl.

| | |
|---|---|
| *A61K 31/44* | (2006.01) |
| *A61K 31/38* | (2006.01) |
| *A61K 31/235* | (2006.01) |
| *A61K 31/4436* | (2006.01) |
| *A61K 31/4402* | (2006.01) |
| *A61K 31/24* | (2006.01) |

(52) U.S. Cl.
CPC ........... *A61K 31/4436* (2013.01); *A61K 31/235* (2013.01); *A61K 31/24* (2013.01); *A61K 31/4402* (2013.01)

(58) Field of Classification Search
CPC .. A61K 31/4436; A61K 31/44; A61K 31/216
USPC ................................. 514/337, 346, 447, 532
See application file for complete search history.

(56) References Cited

FOREIGN PATENT DOCUMENTS

| | | |
|---|---|---|
| KR | 10-0832750 B1 | 5/2008 |
| KR | 10-0860539 B1 | 9/2008 |

OTHER PUBLICATIONS

International Search Report for PCT/KR2013/001122.

*Primary Examiner* — Shengjun Wang
(74) *Attorney, Agent, or Firm* — Harness, Dickey & Pierce, P.L.C.

(57) ABSTRACT

The present invention relates to a pharmaceutical composition for preventing or treating tuberculosis, comprising: (a) a pharmaceutically effective amount of a compound represented by the following chemical formula 1; and (b) a pharmaceutically acceptable carrier. Chemical formula 1 The compound contained as an active ingredient of the present invention inhibits the expression and activity of CO-DH in tubercle *bacillus* so as to effectively block the detoxification of carbon monoxide, which is an important survival factor of tubercle *bacillus*, and is safe for the human body since the compound targets CO-DH which does not exist in the human body. In addition, the compound creates a synergistic effect when combined with a conventional tuberculostatic drug, and thus can be more effective for treating tuberculosis.

8 Claims, 14 Drawing Sheets

FIG. 3

```
Wild Type    MTTADVIEDKETADNDKKPCCYGRMLRKEDPRFIRGRGNYVDDVQLPGMIHLAILRSPFA  60
cutA- mutant MTTADVIEDKETADNDKKPCCYGRMLRKEDPRFIRGRGNYVDDVQLPGMIHLAILRSPFA  60
             ************************************************************

Wild Type    HANIVSVDISAAQAHPKVKLVVIGAMLAEKGLAVMPTLSNDVQAVLATDRVRFQGQEVAF 120
cutA- mutant HANIVSVDI---------------------------------------------------  69
             *********

Wild Type    VVAEDRYSARDALELIDVEYEALDPVIDVRKALDPGAEVIRTDLEGKTDNHCFDVETGDA 180
cutA- mutant ------------------------------------------------------------

Wild Type    AATDAAFAKADVVVTQEIIYPRVHPCPMETCGAVADLDPVSGKLRLVSTIQAPHAHRTLY 240
cutA- mutant ------------------------------------------------------------

Wild Type    ALVAGLPEHKIQVISPDIGGGFGNKVPIYPGYVCAIVGSLLLGKPVKWMEDRAEHLMSTG 300
cutA- mutant ------------------------------------------------------------

Wild Type    FARDYVMLGEIAATKDGKILAIRSNVLADHGAFNGTAAPVKYPAGFFGVFTGSYDIEAAY 360
cutA- mutant ------------------------------------------------------------

Wild Type    CHMTAVYTNKAPGGVAYACSFRITEAVYFVERLVDCLAFDLRMDPVELRLRNLLKPEQFP 420
cutA- mutant ------------------------------------------------------------

Wild Type    YKSKTGVVYDSGDYEKTLRLAMDMIGYDGLRKEQAEKRARGELMGIGVSFFTEAVGAGPR 480
cutA- mutant ------------------------------------------------------------

Wild Type    KDMDILGLGMADGCELRVHPTGKAVVRLSVQTQGQGHETTFAQIVAEELGIPPEDIDVVK 540
cutA- mutant -----------------------------------------------------DVVK   73

Wild Type    GDTDQTPFGLGTYGSRSTPVSGAAAALVARKVRDKAKIIASGMLEASVADLEVEKGSFRV 600
cutA- mutant GDTDQTPFGLGTYGSRSTPVSGAAAALVARKVRDKAKIIASGMLEASVADLEVEKGSFRV 133
             ************************************************************

Wild Type    KGDPAASVTIQDIAMRAHGAADLPEGLEGGLDAQVCYNPENMTYPYGAYFCVVDVDPGTA 660
cutA- mutant KGDPAASVTIQDIAMRAHGAADLPEGLEGGLDAQVCYNPENMTYPYGAYFCVVDVDPGTA 193
             ************************************************************

Wild Type    QVKVRRFLAVDDCGTRINPMIIEGQVHGGIVDGIGMALMEMIAFDEQGNCLGGSLMDYLI 720
cutA- mutant QVKVRRFLAVDDCGTRINPMIIEGQVHGGIVDGIGMALMEMIAFDEQGNCLGGSLMDYLI 253
             ************************************************************

Wild Type    PTAMEVPHFETGHTVTPSPHHPIGAKGVGESATVGSPPAVVNAVVDALAFFGVRHADMPL 780
cutA- mutant PTAMEVPHFETGHTVTPSPHHPIGAKGVGESATVGSPPAVVNAVVDALAFFGVRHADMPL 313
             ************************************************************

Wild Type    NPSRVVEAMQGRATPPI    797  (SEQ ID NO: 6)
cutA- mutant NPSRVVEAMQGRATPPI    330  (SEQ ID NO: 7)
             *****************
```

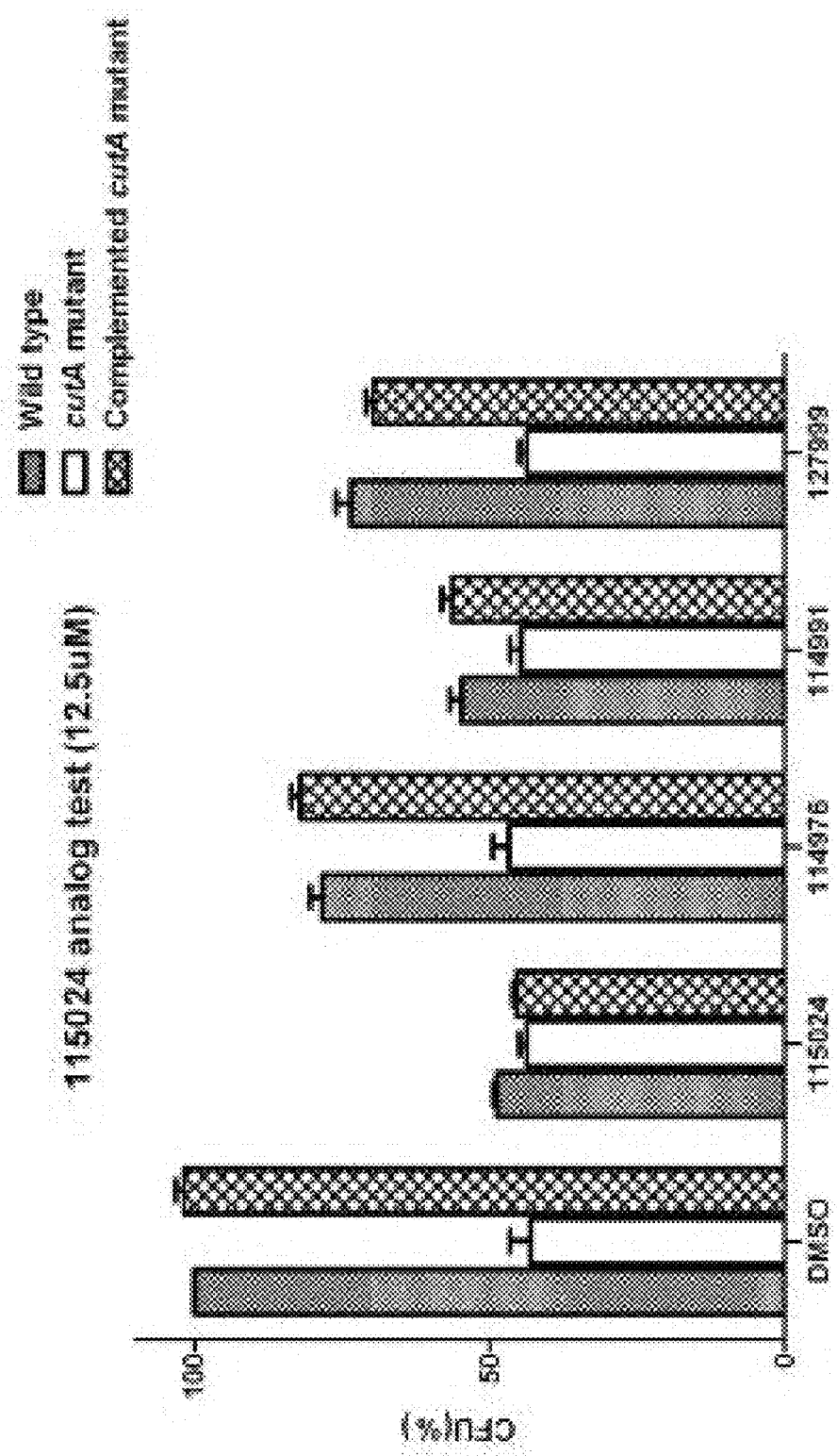

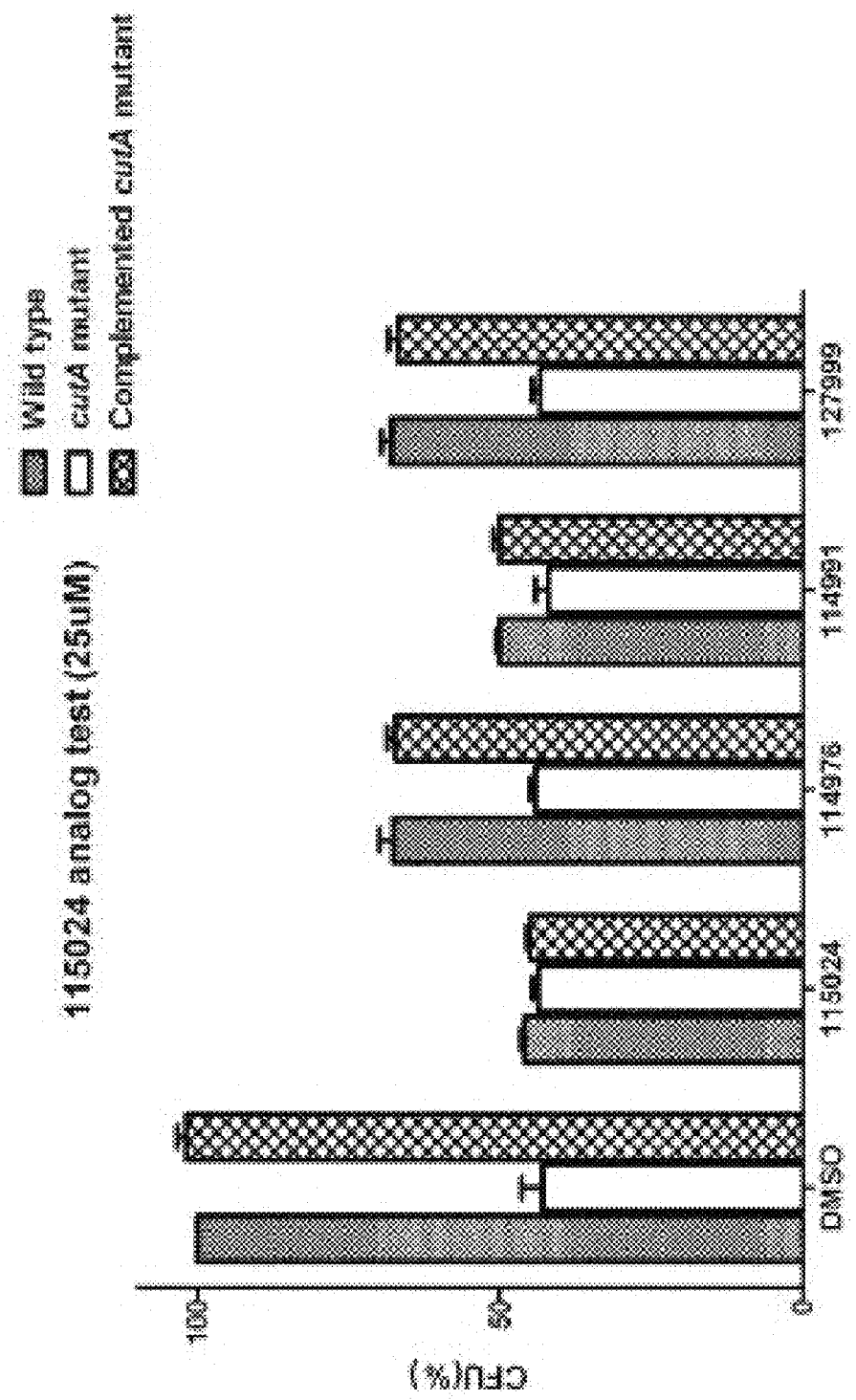

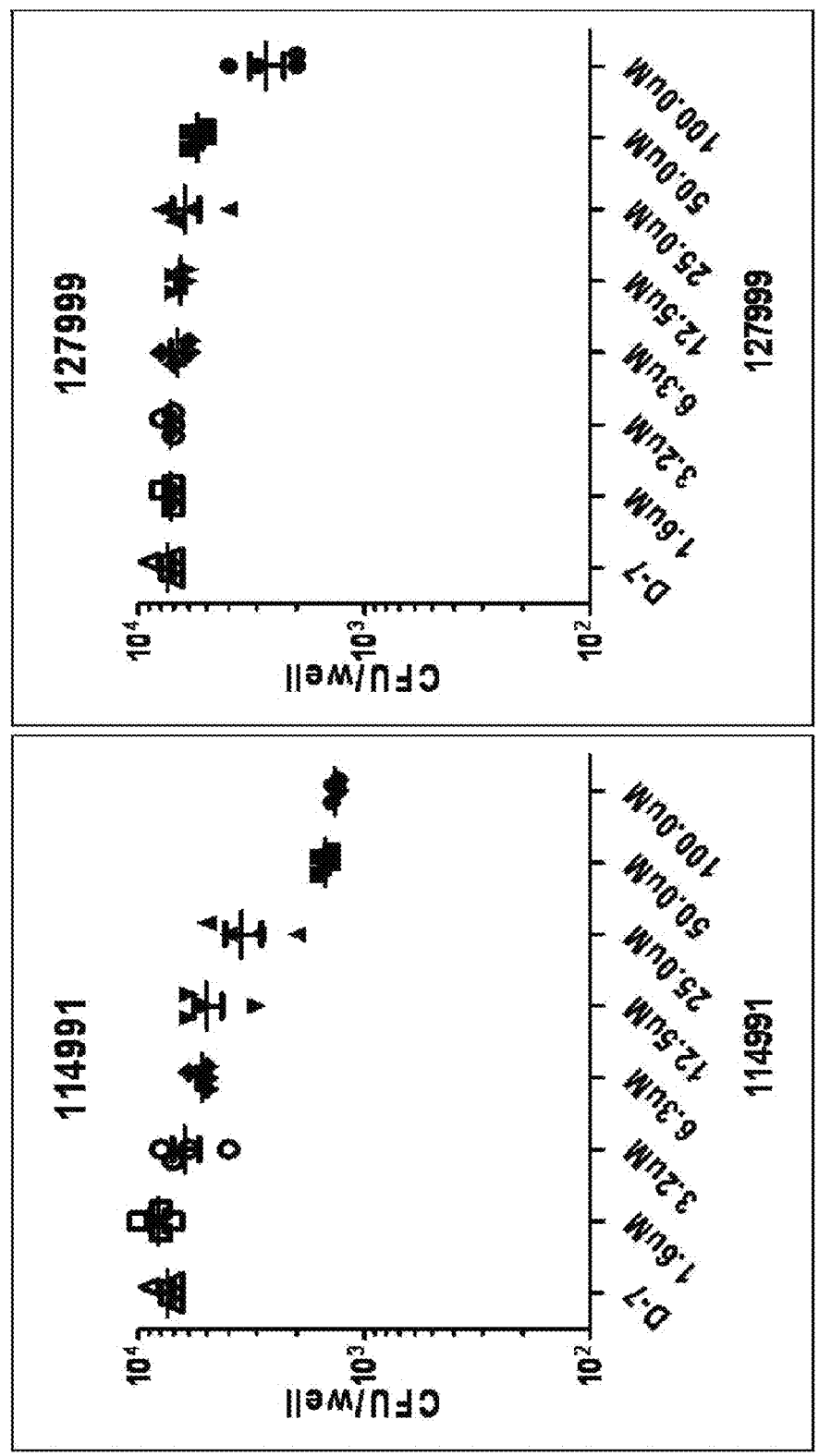

PHARMACEUTICAL COMPOSITION FOR PREVENTING OR TREATING TUBERCULOSIS

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2012/001122, filed 13 Feb. 2013, which claims priority to Korean Patent Application No. 10-2012-0025449, filed Mar. 13, 2012, entire contents of which are incorporated herein by reference.

BACKGROUND

1. Technical Field

The present invention relates to a pharmaceutical composition for preventing or treating tuberculosis based on the inhibition on carbon monoxide dehydrogenase in *Mycobacterium tuberculosis*.

2. Background Art

Tuberculosis is a chronic infectious disease caused by *Mycobacterium tuberculosis*. Tuberculosis is one of the main diseases in developing countries and its seriousness has been increased also in advanced countries. Approximately 8 million new patients are found and approximately 3 million patients die each year. Tuberculosis may be asymptomatic for a considerable period of time even after infection. However, this disease commonly gives rise to acute inflammation of the lungs and then thermal and non-productive cough. Moreover, tuberculosis, if not treated, may typically cause serious complications, leading to death.

Recently, *Mycobacterium tuberculosis* has grown in importance since some cases of infection with *Mycobacterium tuberculosis* strains having resistance against both the HIV pandemic and several kinds of drugs have been reported. According to the researches on antibiotic-resistant *Mycobacterium tuberculosis* over last five years in 35 countries, *Mycobacterium tuberculosis* having resistance to one or more drugs is approaching 36%, and multidrug-resistant *Mycobacterium tuberculosis* (MDR-TB), which shows resistance to two or more antibiotics including rifampin (RMP), is about 36%. These figures indicate serious levels. Approximately 9.9% of patients even without a history of tuberculosis treatment show resistance to at least one drug. As such, drug-resistant tuberculosis and multi-drug resistant tuberculosis increase treatment costs as well as lower treatment efficiency, and eventually become a great threat to patients, such as developing into incurable tuberculosis. The existing tuberculosis treatments generally require a long period of time, one to two years. Here, combined administration of three or four drugs is recommended since the use of one or two antitubercular agents induces fast resistance. However, the long-term use of antitubercular agents strains the liver, causing side effects, such as liver cirrhosis and jaundice. Moreover, for the treatment of multi-drug resistant tuberculosis, secondary antitubercular agents, which are relatively less effective, induce more side effects, and are expensive, need to be used. Accordingly, for the tuberculosis elimination strategy for improving treatment efficiency of the multi-drug resistant tuberculosis, new drugs capable of treating even latent tuberculosis, being more effective, having less side effects, and exhibiting efficacy for a short period of time are required to be developed.

Although antitubercular agents that are harmless to humans, more effective, and act quickly are urgently required to be developed as described above, the currently developed drugs do not exhibit great effects in tuberculosis treatment.

However, the DNA sequence of *Mycobacterium tuberculosis* was established, which opened the possibility to find targets of new drugs. Recently, an inhibitor against expression and activation of carbon monoxide dehydrogenase (CO-DH) is emerging as a new tuberculosis treatment agent.

In general, macrophages inhibit bacterial multiplication through various methods, which include a method in which phagolysosome formed by the fusion of phagosome with lysosome uses protease in the lysosome to remove microorganisms and a method in which bactericidal reactive oxygen and nitrogen species secreted by IFN-γ stimulation remove microorganisms. The reactive nitrogen species is the key material in innate immunity. The reactive nitrogen species contains NO and its derivatives. NO is produced from the degradation of L-arginine by inducible nitric oxide synthase (iNOS). NO derivatives, such as $HNO_2$ and $HNO_3$, play an important role in the control of intracellular parasitic bacteria such as *Mycobacterium tuberculosis* and the like, or cancer cells. Here, *Mycobacterium tuberculosis* survives against various bactericidal mechanisms of macrophages, causing diseases in hosts.

Meanwhile, carboxydobacteria are a group of bacteria which are able to grow by using carbon monoxide (CO) as the sole energy and carbon source. The main enzyme for the oxidation of CO in the carboxydobacteria is CO-DH. CO-DH oxidizes CO into carbon dioxide ($CO_2$) to generate two electrons by using water as an oxidant. Here, $CO_2$ is converted into cellular components through the Calvin cycle, and the electrons are used to energy production through oxidative phosphorylation in the electron transport chain.

It was recently founded that *Mycobacterium* sp. strain JC1, which is evolutionarily far away from the known carboxydobacteria, has CO-DH activity, and CO-DH genes were cloned and DNA-sequenced therefrom. This facilitates the study of CO-DH activities for various species of the genus *Mycobacterium*, and it was found that, besides *Mycobacterium* sp. strain JC1, many species exhibit CO-DH activity. In addition, gene sequencing of some of the previously identified mycobacteria, including *Mycobacterium tuberculosis* H37Rv, revealed that open reading frames (OFRs) similar to those of the CO-DH genes of *Mycobacterium* sp. strain JC1 are conserved in these bacteria. In CO-DH genes of the mycobacteria, three genes seem to be clustered in the order of cutB-cutC-cutA to constitute one operon.

In addition, CO-DH activity on NO was studied from the understanding of structural similarity between CO and NO used as substrates of CO-DH. As a result, it was observed that CO-DH also possesses activity of nitric oxide dehydrogenase (NO-DH) that uses NO as a substrate.

Based on the existing studies, in order to find the relation between NO-DH activity that is exhibited by CO-DH and the intramacrophage survival mechanism of *Mycobacterium tuberculosis*, the present inventors constructed mutants of several species of mycobacteria including *Mycobacterium tuberculosis* H37Rv with respect to CO-DH genes, and established intramacrophage survival-associated characteristics of the mutants.

As a result, in the case of *Mycobacterium tuberculosis* H37Rv, CO-DH activity was observed in only the wild type but not the mutant. Further, it was verified that the intramacrophage survival rate was remarkably reduced in the mutant of *Mycobacterium tuberculosis* H37Rv as compared with the wild type.

These results present a new approach to safe antitubercular agents capable of promoting a complete cure of tuberculosis and reducing tissue damages by inhibiting metabolisms associated with the survival of *Mycobacterium tuberculosis* to suppress survival and growth of *Mycobacterium tuberculosis*.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

SUMMARY

The present inventors endeavored to develop antitubercular agents that are more effective and safer for humans as compared with the existing antitubercular agents. As a result, the present inventors presented CO-DH present in currently unknown *Mycobacterium tuberculosis* for new antitubercular agents, and screened compounds, which inhibit activity and expression of CO-DH to effectively block the detoxification of carbon monoxide as an important factor in the survival of *Mycobacterium tuberculosis*, from the compound libraries. The anti-tuberculosis compounds of the present invention target CO-DH absent in humans and thus are safe for humans, which was verified by a cytotoxicity test. Further, the present inventors verified that the anti-tuberculosis compounds of the present invention create a synergistic effect at the time of combined administration with the existing anti-tuberculosis agents, thereby achieving a more effective treatment of tuberculosis, and thus completed the present invention.

Therefore, the present invention has been made in view of the above-mentioned problems, and an aspect of the present invention is to provide a pharmaceutical composition for preventing or treating tuberculosis.

Another aspect of the present invention is to provide a method for preventing or treating tuberculosis.

Still another aspect of the present invention is to provide a use for preparing a pharmaceutical composition for preventing or treating tuberculosis.

Other purposes and advantages of the present disclosure will become clarified by the following detailed description of invention, claims, and drawings.

BRIEF DESCRIPTION OF THE DRAWINGS

FIG. 3 shows amino acid sequences of intact CutA of *Mycobacterium* sp. strain JC1 wild type and CutA with a deletion of *Mycobacterium* sp. strain JC1 cutA$^-$ mutant. Deleted amino acids were expressed as a line (-).

FIGS. 12a to 12c shows results of survival rates of *Mycobacterium* sp. strain JC1 wild type, and, for CO-DC subunits, cutA mutant and complemented cutA mutant, which were treated with 10 mM of NaNO$_2$ and the compounds of the present invention and then plated on plate media. FIG. 12a shows results for 12.12.5 μM of the compounds of the present invention; FIG. 12b, 25.0 μM; and FIG. 12c, 50 μM.

FIGS. 13a to 13c show results of survival rates of *Mycobacterium tuberculosis* in marrow cell-derived macrophages after treatment with the compounds of the present invention and the control compounds. FIGS. 13a and 13b show results for the compounds of the present invention and FIG. 13c shows results for the control compounds.

DETAILED DESCRIPTION

Figure 1:
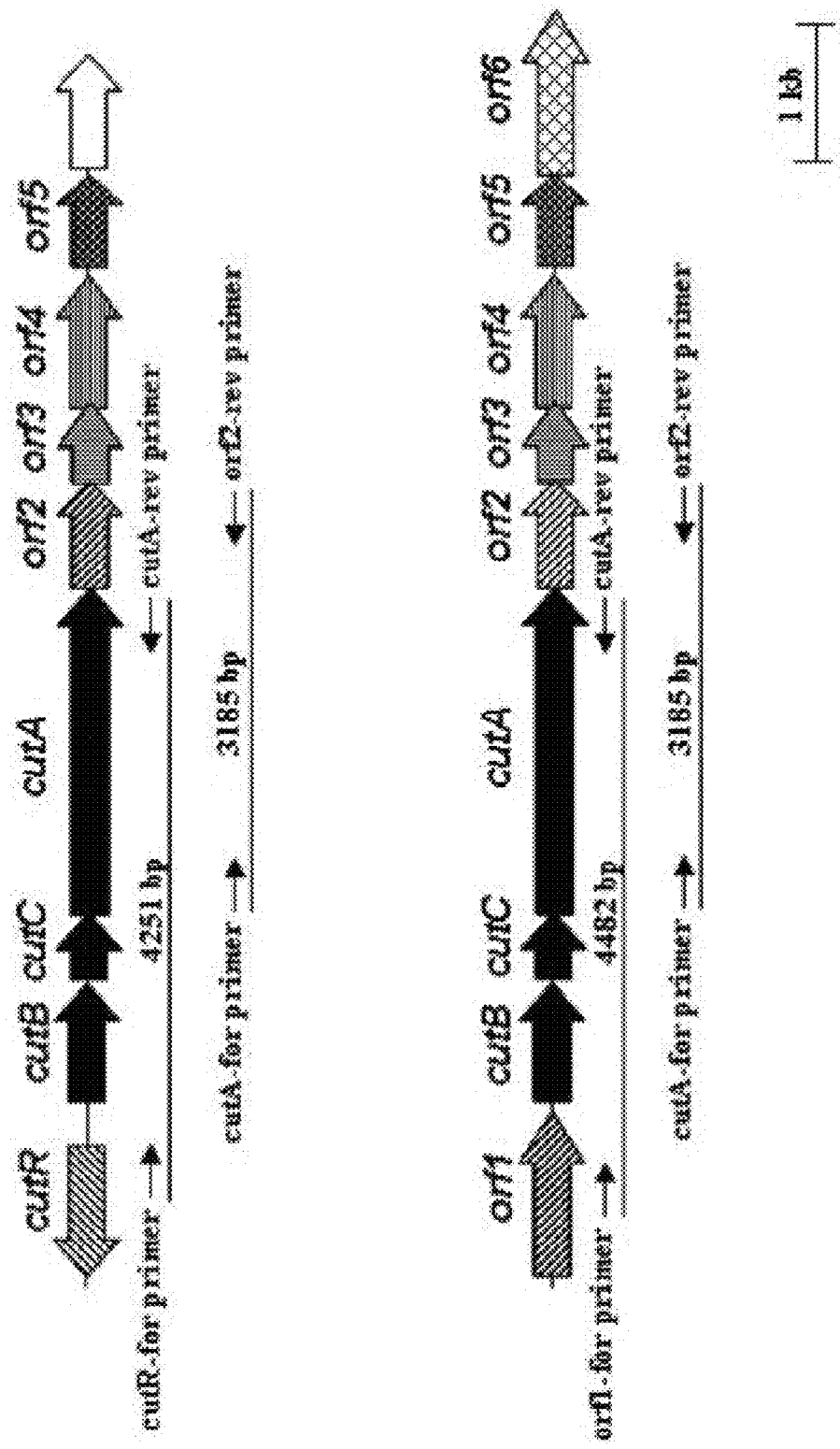
FIG. 1 shows locations of primers used in examples of the present invention.

In accordance with an aspect of the present invention, there is provided a pharmaceutical composition for preventing or treating tuberculosis, the composition including: (a) a pharmaceutically effective amount of a compound represented by Formula 1 below; and (b) a pharmaceutically acceptable carrier:

Formula 1

$$R_1-\underset{H}{N}-\underset{\|}{C}-[CH_2]_n-S-\text{(ring with A, B, }R_2\text{)}$$

wherein in Formula 1, $R_1$ is

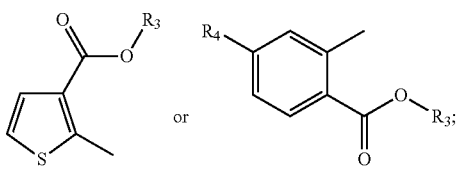

or 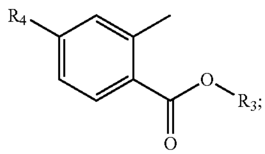 $R_2$ is H, a hydroxyl, halogen, $C_1$-$C_{10}$ alkyl, $C_3$-$C_{15}$ cycloalkyl, $C_2$-$C_{10}$ alkenyl, or $C_1$-$C_8$ alkoxy; A and B each are independently CH or N; and n is an integer of 1 to 5, and wherein in $R_1$, $R_3$ and $R_4$ each are independently H, hydroxyl, halogen, $C_1$-$C_{10}$ alkyl, or $C_3$-$C_{15}$ cycloalkyl.

In accordance with another aspect of the present invention, there is provided a method for preventing or treating tuberculosis, the method including administering to a subject a pharmaceutical composition containing: (a) a pharmaceutically effective amount of a compound represented by Formula 1 above; and (b) a pharmaceutically acceptable carrier.

In accordance with still another aspect of the present invention, there is provided a pharmaceutical composition including: (a) a pharmaceutically effective amount of a compound represented by Formula 1 above; and (b) a pharmaceutically acceptable carrier, for preventing or treating tuberculosis.

In accordance with still another aspect of the present invention, there is provided a use for preparing a pharmaceutical composition for preventing or treating tuberculosis, the composition including: (a) a pharmaceutically effective amount of a compound represented by Formula 1 above; and (b) a pharmaceutically acceptable carrier.

The present inventors endeavored to develop antitubercular agents that are more effective and safer for humans as compared with the existing antitubercular agents. As a result, the present inventors presented CO-DH present in currently unknown *Mycobacterium tuberculosis* for new antitubercular agents, and screened compounds, which inhibit activity and expression of CO-DH to effectively block the detoxification of carbon monoxide as an important factor in the survival of *Mycobacterium tuberculosis*, from the compound libraries. The anti-tuberculosis compounds of the present invention target CO-DH absent in humans and thus are safe for humans, which was verified by a cytotoxicity test. Further, the present inventors confirmed that the anti-tuberculosis compounds of the present invention create a synergistic effect at the time of combined administration with the existing anti-tuberculosis, thereby achieving more effective treatment of tuberculosis, and thus completed the present invention.

The compound used as an active ingredient in the pharmaceutical composition of the present invention is represented by Formula 1. In Formula 1 defining the compound of the present invention, the term "$C_1$-$C_{10}$ alkyl" refers to a straight or branched chain saturated hydrocarbon group having 1 to 10 carbon atoms, and represents preferably "$C_1$-$C_6$ straight or branched chain alkyl", and more preferably "$C_1$-$C_3$ straight or branched chain alkyl", which is a lower alkyl and includes methyl, ethyl, n-propyl, and isopropyl.

As used herein, the term "$C_3$-$C_{15}$ cycloalkyl" refers to a saturated monocyclic or polycyclic hydrocarbon group having 3 to 15 carbon atoms, and includes, for example, a cyclopropyl ring, a cyclobutyl ring, a cyclohexyl ring, a cycloheptyl ring, or the like, but is not limited thereto.

As used herein, the term "$C_2$-$C_{10}$ alkenyl" refers to a straight or branched chain alkenyl having 2 to 10 carbon atoms and at least one carbon-carbon double bond, and includes for example, vinyl, allyl, 2-butenyl, 3-butenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, and the like, but is not limited thereto.

As used herein, the term "$C_1$-$C_8$ alkoxy" includes, for example, methoxy, ethoxy, propoxy, and the like, but is not limited thereto.

As used herein, the term "halogen" includes F, Cl, Br, and I.

According to a preferable embodiment of the present invention, the compound represented by Formula 1 is a compound represented by Formula 2 below:

Formula 2 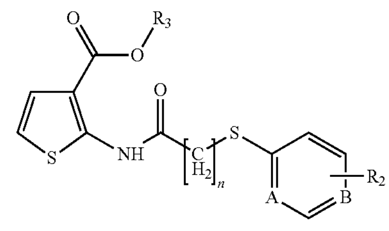 wherein in Formula 2, $R_2$ is H, hydroxyl, halogen, or $C_1$-$C_{10}$ alkyl; A and B each are independently CH or N; n is an integer of 1 to 3; and $R_3$ is H, hydroxyl, halogen, or $C_1$-$C_{10}$ alkyl.

According to another preferable embodiment of the present invention, the compound represented by Formula 1 is a compound represented by Formula 3 below:

Formula 3 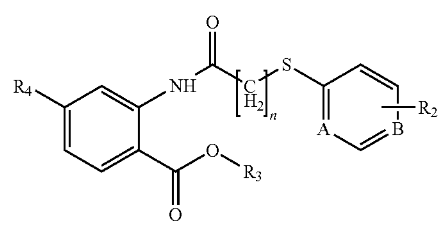 wherein in Formula 3, $R_2$ is H, hydroxyl, halogen, or $C_1$-$C_{10}$ alkyl; A and B each are independently CH or N; n is an integer of 1 to 3; and $R_3$ and $R_4$ each are independently H, hydroxyl, halogen, or $C_1$-$C_{10}$ alkyl.

According to a more preferable embodiment of the present invention, the compound represented by Formula 2 is a compound represented by Formula 4 below:

Formula 4

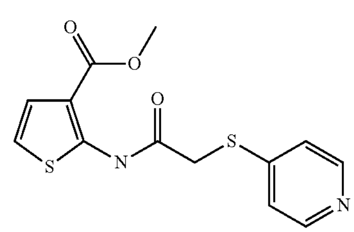

According to still another preferable embodiment of the present invention, the compound represented by Formula 3 is a compound selected from the group consisting of compounds represented by Formulas 5 to 7 below:

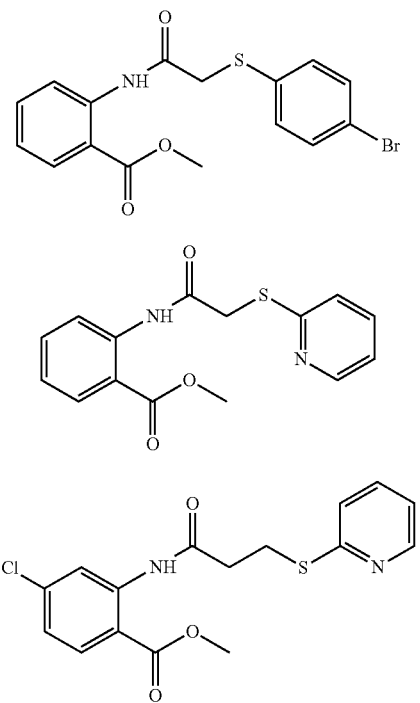

Formula 5

Formula 6

Formula 7

According to still another preferable embodiment of the present invention, the compound which is included as an active ingredient of the present invention inhibits the transcription of CO-DH genes.

According to still another preferable embodiment of the present invention, the compound which is included as an active ingredient of the present invention inhibits the expression of CO-DH genes.

The compound represented by General Formula 1 of the present invention was screened from the representative library and the natural product library (7841 compounds in total) of Korea Chemical Bank by evaluating the inhibition on CO-DH activity through the CO-DH assay. The compound represented by General Formula 1 of the present invention inhibits CO-DH activity of *Mycobacterium tuberculosis* that detoxificates NO and CO generated in microphages.

The test material analyzed by the screening method of the present invention is a single compound or a mixture of compounds (e.g., a natural extract or a cell or tissue culture). The test material may be obtained from a library of synthetic or natural compounds. The method of obtaining the library of such compounds is known in the art. The library of synthetic compounds is commercially available from Maybridge Chemical Co. (UK), Comgenex (USA), Brandon Associates (USA), Microsource (USA) and Sigma-Aldrich (USA), and the library of natural compounds is commercially available from Pan Laboratories (USA) and MycoSearch (USA).

The test material may be obtained through various known combinational library methods known in the art. For example, it may be obtained by a biological library method, a spatially-addressable parallel solid phase or solution phase library method, a synthetic library method requiring deconvolution, a "one-bead one-compound" library method, and a synthetic library method using affinity chromatography selection. The methods of obtaining the molecule libraries are described in DeWitt et al., Proc. Natl. Acad. Sci. U.S.A. 90:6909(1993); Erb et al. *Proc. Natl. Acad. Sci*. U.S.A. 91:11422(1994); Zuckermann et al., *J. Med. Chem.* 37:2678(1994); Cho et al., Science 261:1303(1993); Carell et al., *Angew. Chem. Int.* Ed. Engl. 33:2059(1994); Carell et al., *Angew. Chem. Int.* Ed. Engl. 33:2061; Gallop et al., *J. Med. Chem.* 37:1233(1994); and the like.

According to another preferable embodiment of the present invention, the tuberculosis that is to be prevented or treated by the pharmaceutical composition of the present invention is eye tuberculosis, skin tuberculosis, adrenal tuberculosis, renal tuberculosis, epididymal tuberculosis, lymphatic gland tuberculosis, laryngeal tuberculosis, middle ear tuberculosis, intestinal tuberculosis, multidrug-resistant tuberculosis, pulmonary tuberculosis, sputum tuberculosis, bone tuberculosis, throat tuberculosis, lymphatic tuberculosis, lung deficiency, breast tuberculosis, or spinal tuberculosis.

The composition of the present invention may be more effectively used in the treatment of the above-mentioned tuberculosis through a synergistic effect with the existing antitubercular agents.

As used herein, the term "pharmaceutically effective amount" refers to an amount enough to attain efficacy or activity of the compound of Chemical Formula 1.

When the composition of the present invention is prepared as a pharmaceutical composition, the pharmaceutical composition of the present invention includes a pharmaceutically acceptable carrier. The pharmaceutically acceptable carrier included in the pharmaceutical composition of the present invention is one conventionally used in formulations, and examples thereof may include, but are not limited to, lactose, dextrose, sucrose, sorbitol, mannitol, starch, *acacia* gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further include, besides the above components, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

The pharmaceutical composition of the present invention may be administered orally or parenterally. Examples of parenteral administration may include intravenous injection, subcutaneous injection, intramuscular injection, intraperitoneal injection, transdermal injection, mucosal administration, administration of eye drops, and the like.

A suitable administration dose of the pharmaceutical composition of the present invention may be varied depending on various factors, such as method of formulation, manner of administration, age, body weight, sex, and morbidity of the patient, diet, route of administration, excretion rate, and response sensitivity. Preferably, the suitable administration dose is 0.0001 to 100 mg/kg (body weight) in adults.

The pharmaceutical composition of the present invention may be formulated into a unit or multiple dosages form using a pharmaceutically acceptable carrier and/or excipient according to the method easily conducted by a person having ordinary skill in the art to which the present invention pertains. Here, the dosage form may be a solution in an oily or aqueous medium, a suspension, a syrup, or an emulsion, an extract, a powder, a granule, a tablet, or a capsule, and may further include a dispersant or a stabilizer.

Features and advantages of the present invention are summarized as follows:

(i) The present invention is directed to antitubercular agents containing compounds that inhibit activity and expression of CO-DH to effectively block the detoxification of carbon monoxide as an important factor in the survival of *Mycobacterium tuberculosis*.

(ii) The anti-tuberculosis compounds of the present invention target CO-DH that absent in humans and thus are safe for humans, which was confirmed by a cytotoxicity test.

(iii), Further, the anti-tuberculosis compounds of the present invention create a synergistic effect at the time of combined administration with the existing anti-tuberculosis, thereby achieving more effective treatment of tuberculosis.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

Preparation of *Mycobacterium* sp. Strain JC1 cutA Mutants

1. Methods (1) Construction of Vector for Mutant Preparation

Figure 2:
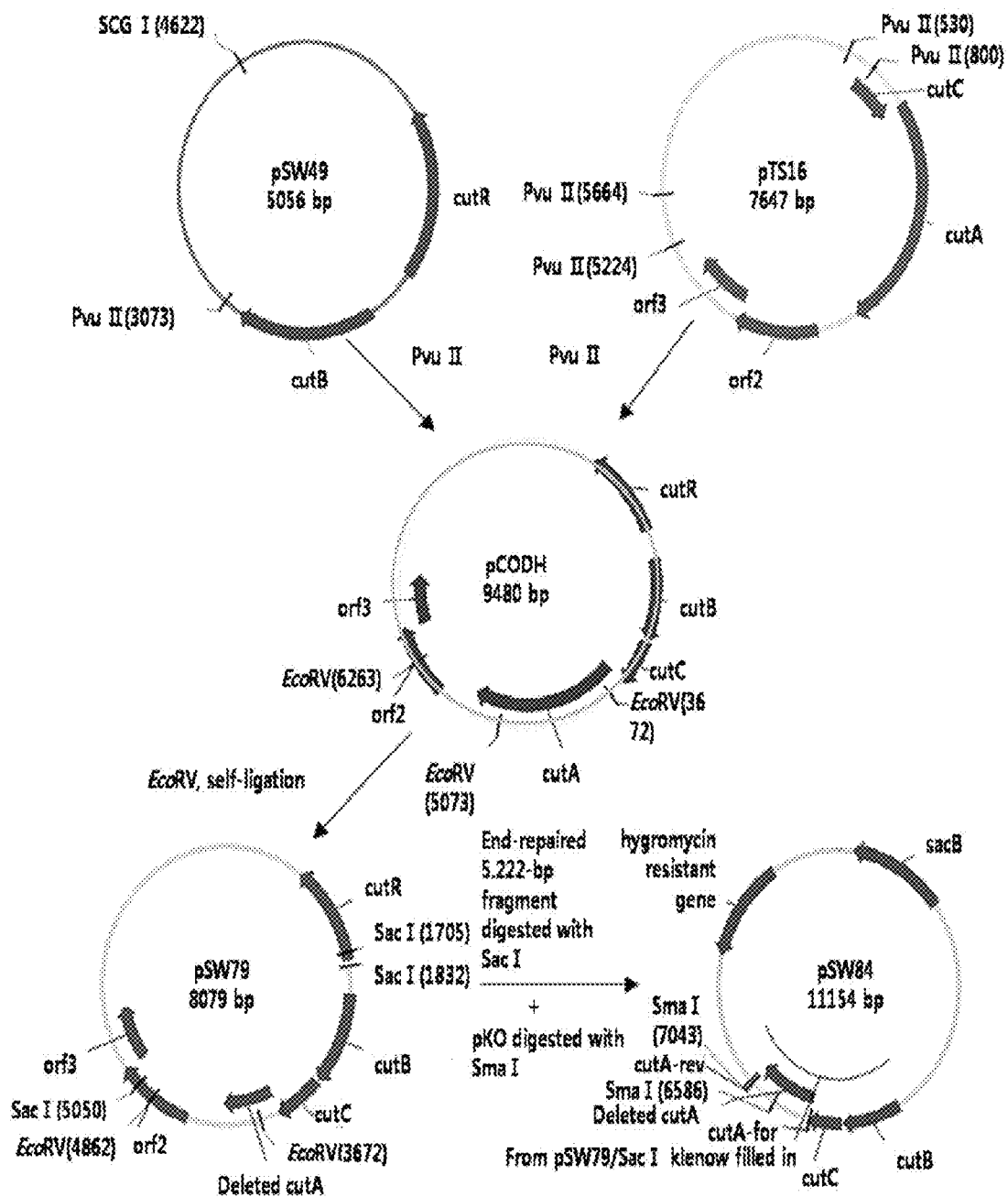
FIG. 2 shows a construction procedure of plasmid pSW84 used in examples of the present invention.

The 2.543-bp DNA fragment prepared by digestion of pTS8 with both of the restriction enzymes PvuII and EcoRV was ligated to pBluescript II SK(+), thereby obtaining pSW49. The 5,056-bp DNA fragment prepared by digestion of the pSW49 with the restriction enzyme PvuII and the 4,424-pb DNA fragment prepared by digestion of pTS16 with the restriction enzyme PvuII were ligated to obtain pCODH. The 6,889-bp and 1,190-bp DNA fragments, which were prepared by digestion of the pCODH with the restriction enzyme EcoRV, were ligated to obtain pSW79 containing the cutA gene with a 1,401-bp in-frame deletion. In order to insert the pSW79 into pKO that contains a hygromycin-resistant gene and a sacB gene and is usable as a suicide vector in *Mycobacterium* sp. strain JC1 (Sherman et al., 2001), the 3,222-bp DNA fragment prepared by digestion of the pSW79 with the restriction enzyme SacI was blunt-ended with the enzyme Klenow, and then inserted into a partial fragment prepared by digestion of the pKO with the restriction enzyme SmaI, thereby obtaining pSW84 (FIG. 2).

(2) Preparation and Verification of Mutants a. Preparation and Isolation of *Mycobacterium* sp. Strain JC1 cutA1$^-$ or cutA2$^-$ Mutant In order to obtain a mutant (cutA1$^-$ or cutA2$^-$) in which one of two cutA genes (cutA1 and cutA2) constituting two copies of CO-DH genes (copy I and copy II) present in *Mycobacterium* sp. strain JC1 has an inframe deletion, competent cells prepared by using wild type *Mycobacterium* sp. JC1 were transformed with pSW84 by electroporation. Then, the transformed strain was plated on the 7H9-glucose solid medium containing hygromycin (76 μg/ml). The culturing was performed at 37° C. for 4 days to obtain a single-crossover mutant. The obtained single-crossover mutant was cultured in the 7H9-glucose liquid medium free from hygromycin at 37° C. and 200 rpm for 7 days, and then 30 μl of the culture liquid was plated on the 7H9 solid medium supplemented with 10% (w/v) sucrose. The culturing was performed at 37° C. for 4 days to obtain a double-crossover mutant.

b. Verification of Mutant with a Deletion in One cutA Gene

In order to verify whether the obtained *Mycobacterium* sp. strain JC1 mutant is cutA1$^-$ mutant or cutA2$^-$ mutant, PCR amplification of chromosomal DNA extracted from the obtained mutant was performed by using primers cutR-for (5'-gagccccgacgacgttcggg-3') and cutA-rev (5'-cagatcg-gcggggtcgctctg-3') or orf1-for (5'-ggcgtgggtatggaggtctt-3') and cutA-rev (5'-cagatcggcggggtcgctctg-3').

In the case of PCR using the primers cutR-for (5'-gagc-cccgacgacgttcggg-3') and cutA-rev (5'-cagatcg-gcggggtcgctctg-3'), the 2,850-bp PCR product, which is shortened by 1,401 bp as compared with the wild type (4,251-bp PCR product), will be produced if mutation occurs in the cutA1 gene. In the case of PCR using the primers orf1-for (5'-ggcgtgggtatggaggtctt-3') and cutA-rev (5'-cagatcg-gcggggtcgctctg-3'), the 3,081-bp PCR product, which is shortened by 1,401 bp as compared with the wild type (4,482-bp PCR product), will be produced if mutation occurs in the cutA2 gene.

c. Preparation and Isolation of *Mycobacterium* sp. Strain JC1 cutA1$^-$/A2$^-$ Mutant Competent cells prepared by using the mutant in which mutation occurs in one cutA gene were transformed with pSW84 by electroporation. Then, the transformed strain was plated on the 7H9-glucose solid medium containing hygromycin (75 μg/ml). The culturing was performed at 37° C. for 4 days to obtain a single-crossover mutant. The obtained single-crossover mutant was cultured in the 7H9-glucose liquid medium free from hygromycin at 37° C. and 200 rpm for 7 days, and then 30 μl of the culture liquid was plated on the 7H9 solid medium supplemented with 10% (w/v) sucrose. The culturing was performed at 37° C. for 4 days to obtain a double-crossover mutant.

d. Verification of *Mycobacterium* sp. Strain JC1 cutA1$^-$/A2$^-$ Mutant

In order to confirm *Mycobacterium* sp. strain JC1 cutA1$^-$/A2$^-$ mutant, PCR amplification of chromosomal DNA extracted from the obtained mutant was performed by using primers cutA-for (5'-gcatgacgactgcagacgtta-3') and orf2-rev (5'-gtcactcgtgaccgcagcat-3'), which are commonly present in copy I and copy II of CO-DH genes. Only the 1,784-bp PCR product, which is shortened by 1,401 bp as compared with the wild type (3,185-bp PCR product), will be produced if mutation occurs in both the cutA1 and cutA2 genes. Both of the 3,185-bp PCR product and 1,784-bp PCR product will be produced for the *Mycobacterium* sp. strain JC1 cutA1 or cutA2 mutant.

2. Results

1) Construction of Vector for Mutant Induction

The vector pSW84 for inducing a mutant having a 1,401-bp inframe deletion in the cutA gene as compared with the wild type cutA gene was constructed (FIG. 2). The portion which is deleted from the vector for mutant induction, pSW84, contains a binding region of cutA with molybdopterin cytosine dinucleotide (MCD), which is considered to be important in the binding with CO, and a binding region of cutA genes for a dimer structure (Dobbek et al., 1999) (FIG. 3). Thus, *Mycobacterium* sp. strain JC1 cutA1$^-$/A2$^-$ mutant is determined to be impaired since cutA genes do not constitute a dimer structure and the binding with CO is impossible.

Figure 4:
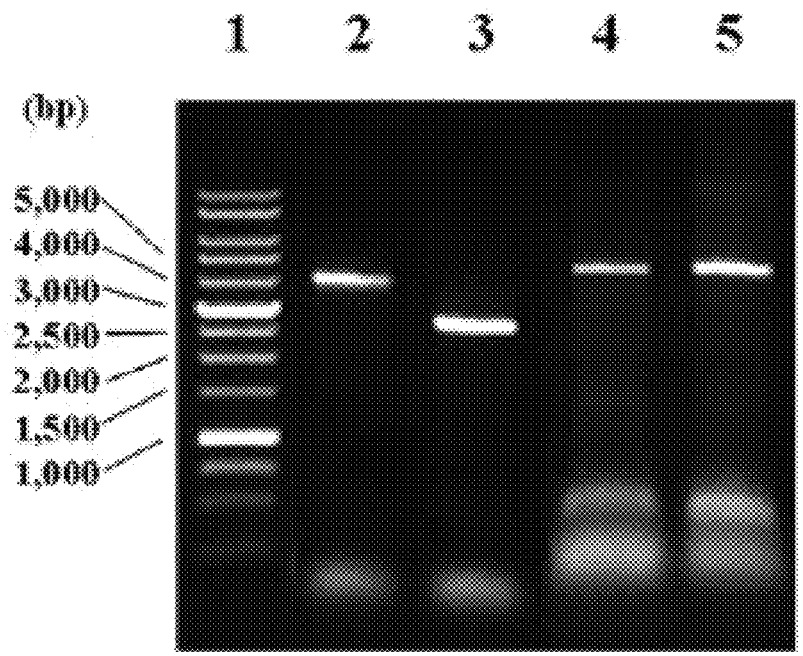
FIG. 4 shows a gel image of *Mycobacterium* sp. strain JC1 cutA1$^-$ mutant confirmed by PCR. Lane 1 represents 1-kb ladder; Lane 2, 4,251-bp PCR product obtained from chromosomal DNA of *Mycobacterium* sp. strain JC1 wild type by using primers cutR-for and cutA-rev; Lane 3, 2,850-bp PCR product obtained from chromosomal DNA of *Mycobacterium* sp. strain JC1 cutA1$^-$ mutant by using primers cutR-for and cutA-rev; Lane 4, 4,482-bp PCR product obtained from chromosomal DNA of *Mycobacterium* sp. strain JC1 wild type by using primers orf1-for and cutA-rev; and Lane 5, 4,482-bp PCR product obtained from chromosomal DNA of *Mycobacterium* sp. strain JC1 cutA1$^-$ mutant by using primers orf1-for and cutA-rev.

2) Isolation and Verification of *Mycobacterium* sp. Strain JC1 cutA1$^-$ Mutant A mutant with a deletion in one cutA gene, which was obtained by introducing the prepared pSW84 into the *Mycobacterium* sp. strain JC1 wild type through electroporation, was isolated. In order to verify whether the isolated mutant is cutA1$^-$ mutant or cutA2$^-$ mutant, PCR amplification of chromosomal DNA extracted from the isolated mutant was performed. The 2,850-bp PCR product was obtained for the primers cutR-for (5'-gagccccgacgacgttcggg-3') and cutA-rev (5'-cagatcggcggggtcgctctg-3') and the 4,482-bp PCR product was obtained for the primers orf1-for (5'-ggcgtgggtatggaggtctt-3') and cutA-rev (5'-cagatcggcggggtcgctctg-3'). Thus, it was verified that the isolated mutant was cutA1⁻ mutant (FIG. 4) This result was again verified by cloning of the PCR product into the pGEM T-easy vector and sequencing thereof.

Figure 5:
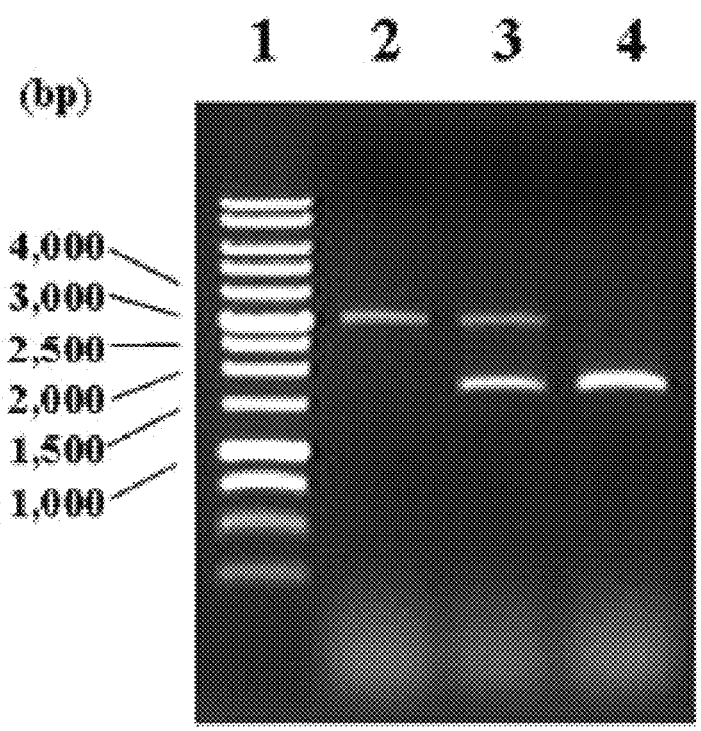
FIG. 5 shows a result of *Mycobacterium* sp. strain JC1 cutA1$^-$/A2$^-$ mutant confirmed by PCR. Lane 1 represents 1-kb ladder; Lane 2, 3,185-bp PCR product obtained from chromosomal DNA of *Mycobacterium* sp. strain JC1 wild type by using primers cutA-for and orf2-rev; Lane 3, 3,185-bp and 1,784-bp PCR products obtained from chromosomal DNA of *Mycobacterium* sp. strain JC1 cutA1$^-$ mutant by using primers cutA-for and orf2-rev; and Lane 4, 1,784-bp PCR product obtained from chromosomal DNA of *Mycobacterium* sp. strain JC1 cutA1$^-$/A2$^-$ mutant by using primers cutA-for and orf2-rev.

3) Isolation and Verification of *Mycobacterium* sp. Strain JC1 cutA1⁻/A2⁻ Mutant The cutA1⁻/A2⁻ mutant was isolated by introducing of the prepared pSW84 into the cutA1⁻ mutant by electroporation. In order to verify whether the isolated mutant is the cutA1⁻/A2⁻ mutant with a deletion in both two cutA genes, PCR amplification of chromosomal DNA extracted from the isolated mutant was performed. Only the 1,784-bp PCR product, which was shortened by 1,401 bp as compared with the 3,185-bp PCR product, was obtained for the primers cutA-for (5'-gcatgacgactgcagacgtta-3') and orf2-rev (5'-gtcactcgtgaccgcagcat-3'). Thus, it was verified that the isolated mutant was cutA1⁻/A2⁻ mutant (FIG. 5) This result was again verified by cloning of the PCR product into the pGEM T-easy vector and sequencing thereof.

Figure 6:
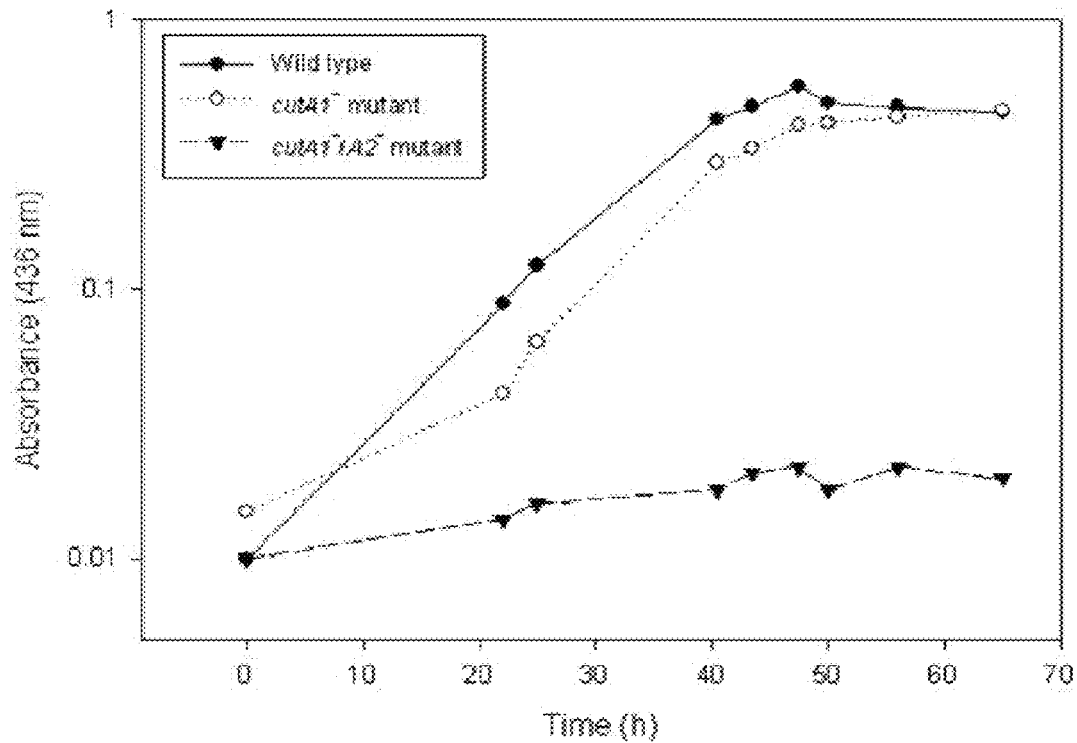
FIG. 6 shows growth curves of *Mycobacterium* sp. strain JC1 wild type (●), cutA1$^-$ mutant (○), and cutA1$^-$/A2$^-$ mutant (▼).
Figure 7:
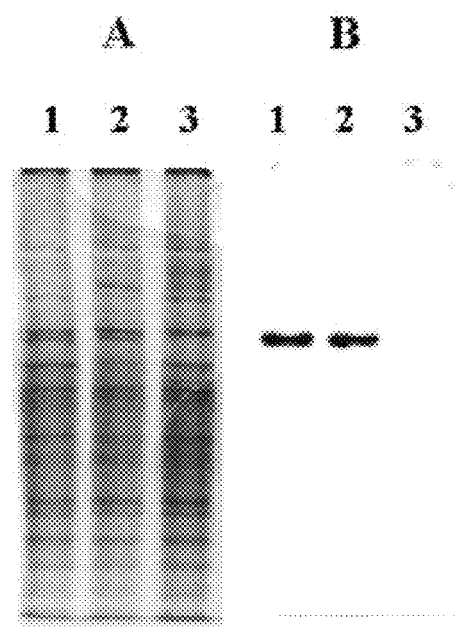
FIG. 7 shows results of staining based on CO-DH activity for cell extracts of *Mycobacterium* sp. strain JC1 wild type (Lane 1), cutA1$^-$ mutant (Lane 2), and cutA1$^-$/A2$^-$ mutant.
Figure 8:
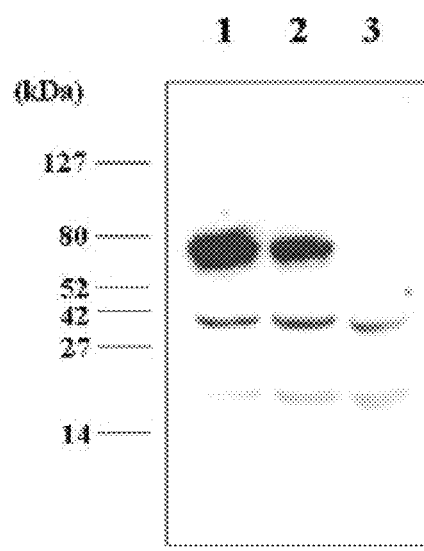
FIG. 8 shows results of western blotting of *Mycobacterium* sp. strain JC1 wild type (Lane 1), cutA1$^-$ mutant (Lane 2), and cutA1$^-$/A2$^-$ mutant (Lane 2).

Further, it was verified that the *Mycobacterium* sp. strain JC1 cutA1⁻/A2⁻ mutant was not grown in the SMB-CO medium (FIG. 6). Further, the cell extract of the cutA mutant grown in the SMB-glucose medium was subjected to staining based on CO-DH activity (FIG. 7) and western blotting (FIG. 8), and as a result, it was verified that CutA was absent and thus CO-DH activity was not exhibited in the cutA1⁻/A2⁻ mutant.

4) Complementation Test of cutA Mutant

Figure 9:
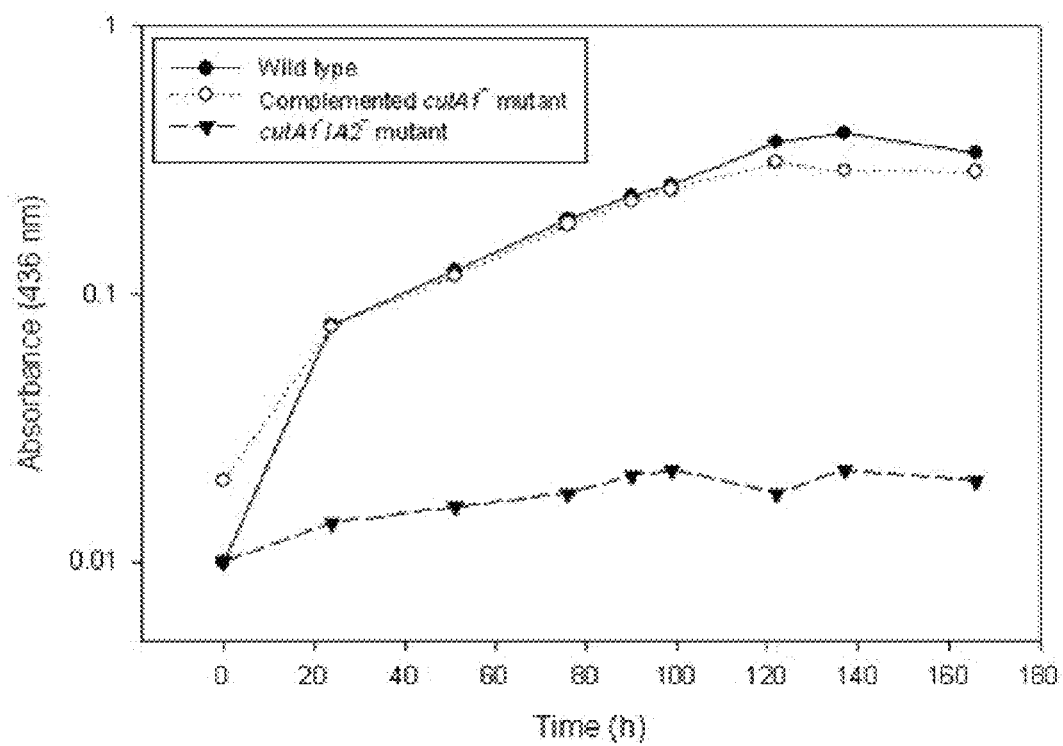
FIG. 9 shows growth curves of *Mycobacterium* sp. strain JC1 wild type (●), cutA1$^-$/A2$^-$ mutant (▼), and complemented cutA1$^-$/A2$^-$ mutant (○).
Figure 10:
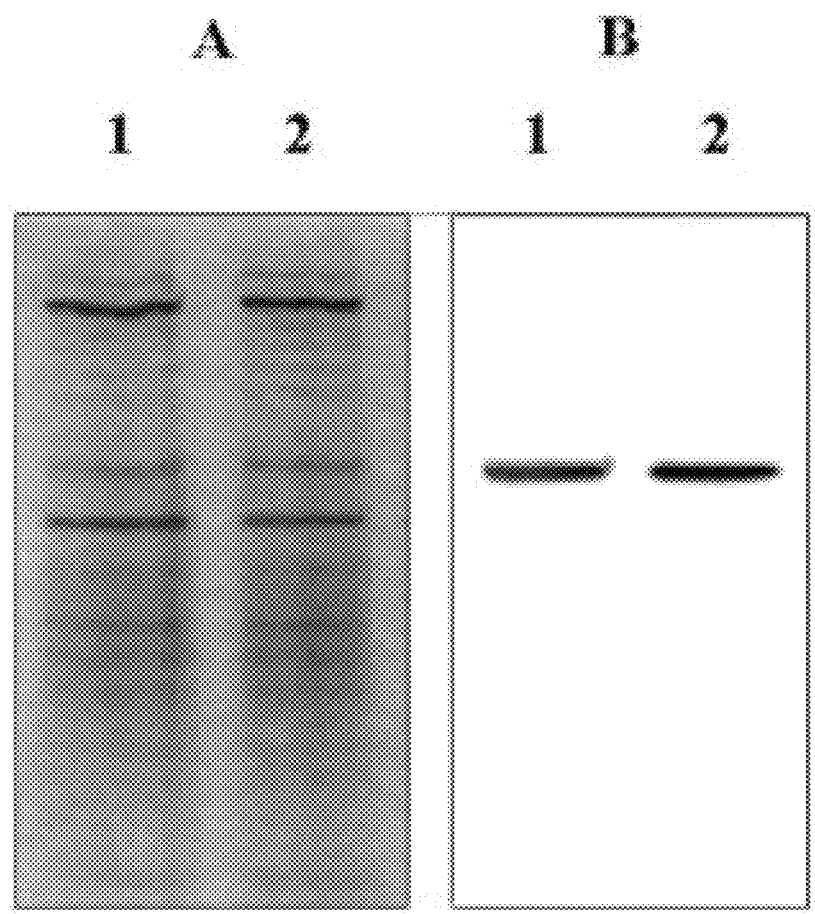
FIG. 10 shows results of staining based on CO-DH activity of *Mycobacterium* sp. strain JC1 wild type (Lane 1) and complemented cutA1$^-$/A2$^-$ mutant (Lane 2) grown in the SMB-CO medium.

The obtained *Mycobacterium* sp. strain JC1 cutA1⁻/A2⁻ mutant was complemented by the pTWMA-JC1 (Jung, 004) with cutA gene of *Mycobacterium* sp. strain JC1. As a result, it was verified that the complemented mutant was grown in the SMB-CO medium (FIG. 9). The complemented mutant was grown in the SMB-glucose medium and then subjected to staining based on CO-DH activity. As a result, it was verified that the complemented mutant possessed CO-DH activity (FIG. 10).

Example 2

Screening of Compounds Through CO-DH Activity Measurement (1) Library Compounds

The inhibition of CO-DH activity was measured for the representative library and the natural product library (7841 compounds in total) of Korea Chemical Bank by three times of CO-DH activity assay for each compound. The measured values were averaged. The results were shown FIG. 11.

Figure 11:
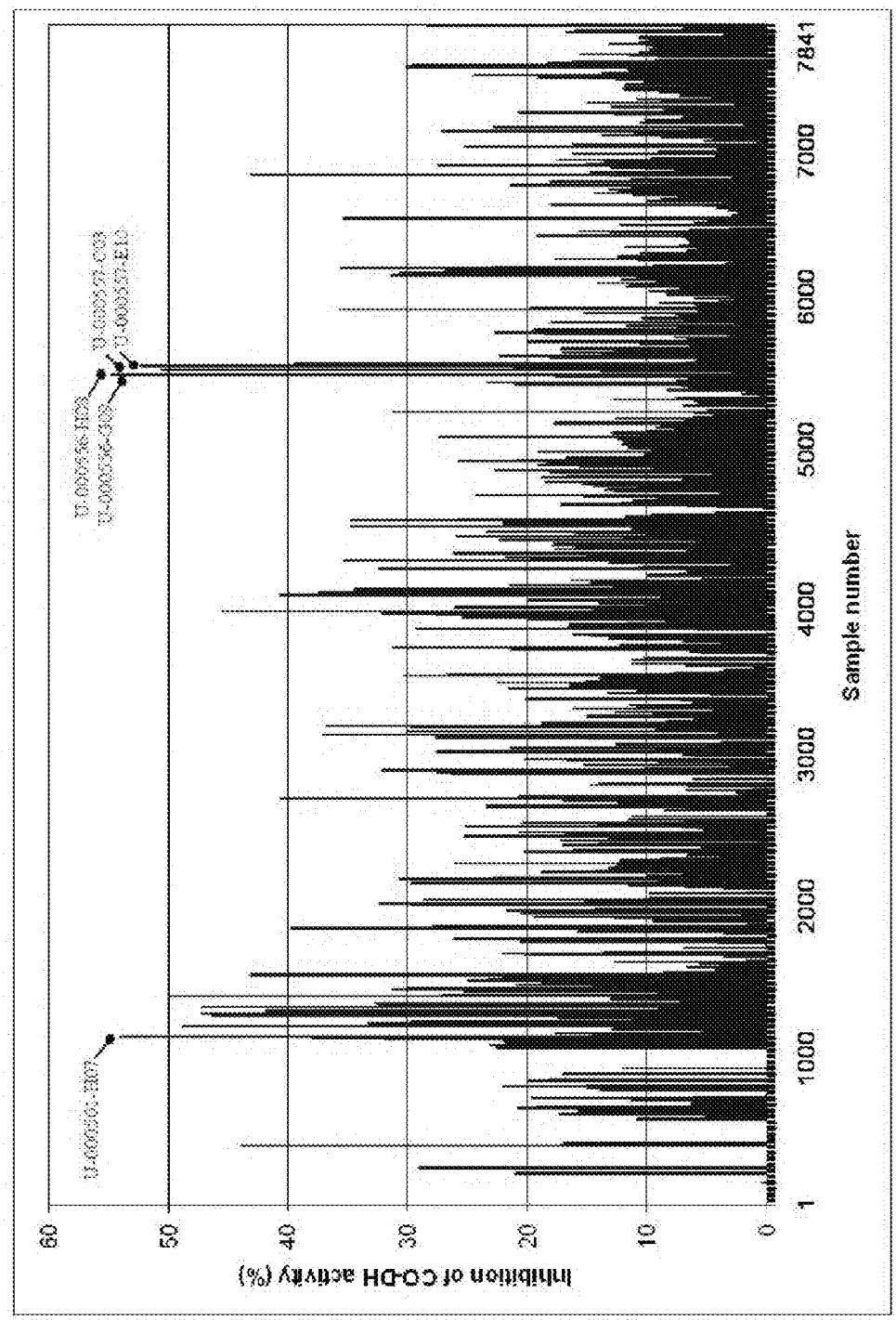
FIG. 11 shows results of the inhibition on CO-DH activity for libraries of Korea Chemical Bank.

As can be seen from FIG. 11, many kinds of compounds of the compound libraries exhibited the inhibitory effect on CO-DH activity. Among them, Compound 115024 represented by Chemical Formula 1 below was selected as being most effective in tests on the inhibition of enzyme activity and the inhibition of bacteria. After that, its analogs were assayed and approximately 200 kinds of compounds were again provided. Among them, three most effective compounds (114976, 114991, and 127999) were selected wherein the three compounds are represented by Chemical Formulas 2 to 4, respectively:

Chemical Formula 1

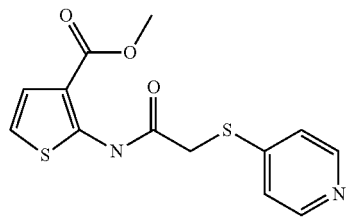

Chemical Formula 2

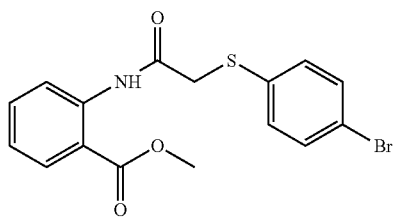

Chemical Formula 3

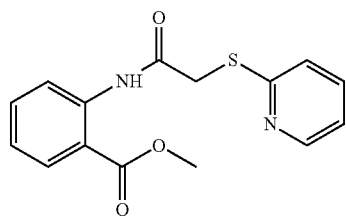

Chemical Formula 4

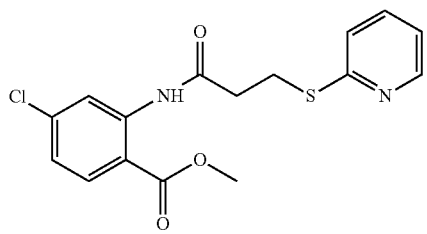

(2) Extraction of Protein

In order to obtain an enzyme extract to be used for the measurement of CO-DH activity, the bacteria cultured according to respective experiment conditions were collected by centrifugation at 18,000×g for 10 minutes at 4° C. (Eppendorf centrifuge-5403, Hamburg, Germany), washed twice with a 50 mM Tris-HCl (pH 7.5) buffer solution, and re-suspended in 3 and of a 50 mM Tris-HCl (pH 7.5) buffer solution. The suspended bacteria were homogenized at 0° C. by repeating 20 times of ultrasonication using an ultrasonic processor (Sonics & Materials Inc., Danbury, Conn.) wherein the ultrasonication was conducted such that ultrasonic wave at 20% amplitude was applied for 3 seconds and paused for 10 seconds. The homogenized culture solution was collected by centrifugation at 18,000×g for 30 minutes at 4° C. (Eppendorf centrifuge-5403), and a supernatant was used as an enzyme extract.

(3) Quantification of Protein

Proteins were quantified using bovine serum albumin (BSA) as a standard protein according to the method of Bradford (1976).

(4) Measurement of CO-DH Activity

CO-DH activity was determined by measuring the reduction rate of 2-(4-indophenyl)-3-(4-nitrophenyl)-2H-tetrazolium chloride (INT, Sigma, $\epsilon_{496}=17.981$ mM$^{-1}$ cm$^{-1}$) in the presence of CO. Here, 1-methoxyphenazine methosulfate (MPMS, Sigma) was used as an electron transfer mediator between CO-DH and INT. A mixture solution of 19.2 ml of 50 mM Tris-HCl (pH 7.5), 250 µl of INT (9.8 mM), 50 µl of MPMS (8.9 mM), and 500 µl of Triton X-100 (25%, v/v) was saturated with CO gas. 800 µl of the resultant solution was added into a plastic cuvette, and then each compound was added thereto to a final concentration of 12.5 µM. Last, 800 µl of the enzyme extract was added thereto, followed by reaction at 30° C. for 200 seconds. Here, the absorbance change is due to red formazan generated resulting from INT reduction, and was measured at 496 nm by using a spectrophotometer (U-2000, Hitachi) equipped with a temperature adjuster. Enzyme specific activity was expressed as nmoles of reduced INT per mg of protein per minute (nmol/mg protein/min). The enzyme specific activity of each compound treatment group was expressed as a percentage of the control group of which enzyme specific activity was set to 100%, and the results were summarized in Table 1.

TABLE 1

| Concentration | Inhibition of CO-DH activity 12.5 µM |
|---|---|
| Compound 1 (115024) | 48 |
| Compound 2 (114976) | 18 |
| Compound 3 (114991) | 15 |
| Compound 4 (127999) | 7 |

As can be verified from Table 1 above, the compound of Chemical Formula 1 was the most effective in the inhibition of CO-DH activity, followed by the compounds of Chemical Formulas 2, 3, and 4 in that order.

(5) Measurement of Survival Rate

In order to measure the survival rate against $NaNO_2$ for each bacterium, the modification of KATSUMASA SATO method (1992) was conducted. Experiment groups and the control group were cultured for 12 hours. The experimental groups were prepared by adding 10 mM $NaNO_2$ and a CO-DH inhibitor to the bacteria cultured to the mid-exponential growth phase in the SMB-glucose medium (pH 5.5). The control group were prepared by dissolving 10 mM $NaNO_2$ and a CO-DH inhibitor in a solvent (DMSO) to the bacteria. The experimental groups and control groups were appropriately diluted, and then plated on the SMB-glucose solid medium. The colony forming unit (CFU) value was calculated based on the number of obtained colonies. The calculated CFU value was expressed as a percentage of the control group. The results were shown in FIGS. 12a to 12c below.

Figure 12C:
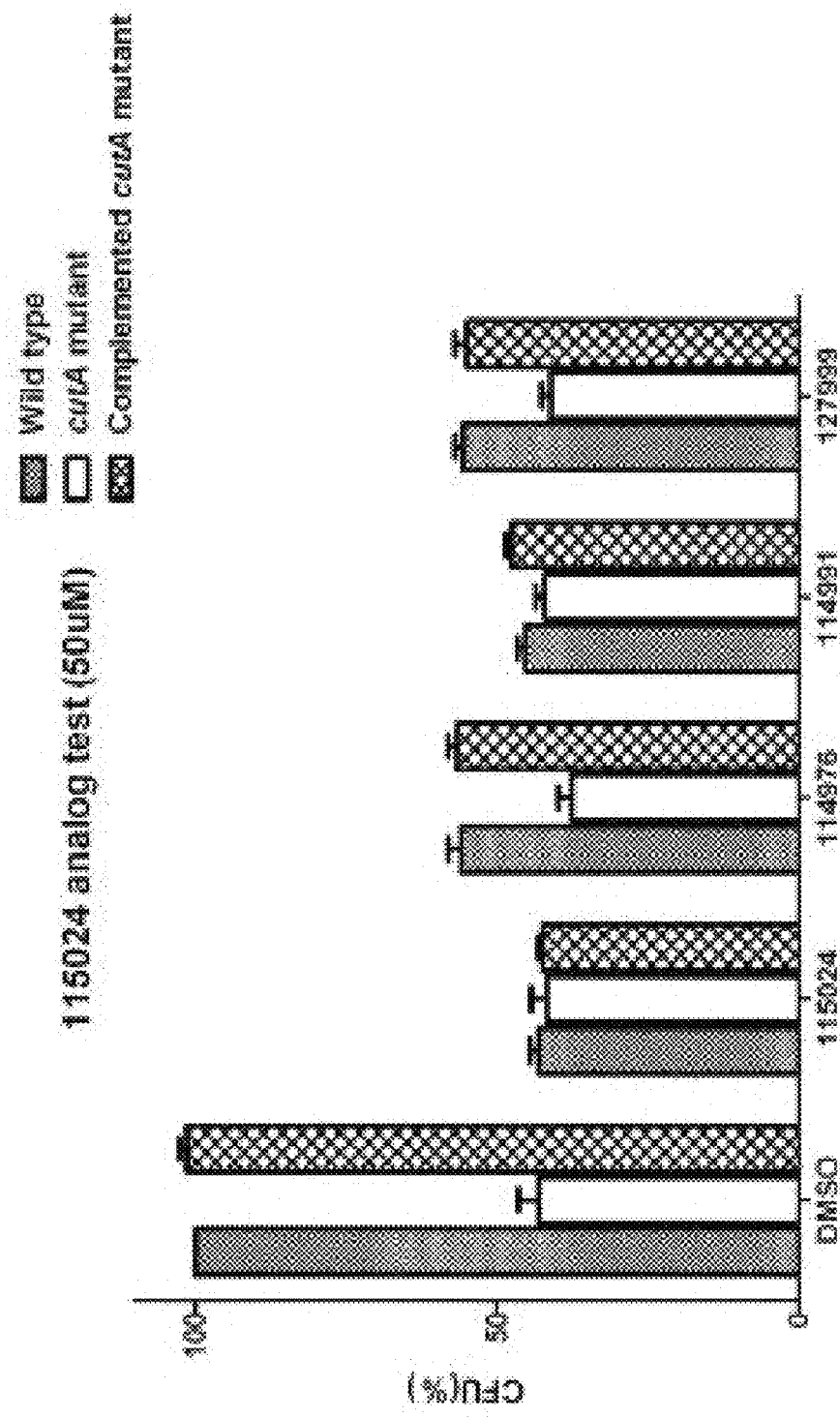

As can be seen from FIGS. 12a to 12c below, the survival rate of the *Mycobacterium* sp. strain JC1 wild type was reduced in a concentration-dependent manner when treated with the compounds of Chemical Formulas 1 to 4 of 12.5 µM to 50 µM. It can be seen from the above results of compound treatment that the survival rate reduction of *Mycobacterium* sp. strain JC1 wild type was similar to that of the *Mycobacterium* sp. strain JC1 cutA mutant.

Example 3

Anti-Tuberculosis Test of Compounds

The anti-tuberculosis test of compounds was conducted using in an ex vivo binding model. Macrophages derived from mouse bone marrow cells were cultured and then infected with tuberculosis standard strain, followed by administration of each compound of different concentrations. The viable cell count of *Mycobacterium tuberculosis* remaining after culturing for 1 hour was measured for each of the compounds, and then compared with that of the control group.

The tuberculosis standard strain *Mycobacterium tuberculosis* H37Rv was seeded in 5 ml of the Middlebrook 7H9 (Difco) liquid medium, followed by culturing for 1 week; 5 ml of the culture liquid of *Mycobacterium tuberculosis* was seeded in 50 ml of the 7H9 medium, followed by culturing for 1 week; and 50 ml of the resultant culture liquid was seeded in 200 ml of the 7H9 medium, followed by culturing for 4 days. Then, the resultant culture liquid was left for 30 minutes, and only the supernatant was taken. A solution of glycerin was added thereto to a concentration of 10%, and then frozen-stored. The next day, the viable cell count of *Mycobacterium tuberculosis* under freezing storage was measured by ten-fold serial dilution. The *Mycobacterium tuberculosis* liquid under freezing storage was diluted with the Middlebrook 7H9 medium at a dilution ratio of 10,000 fold, 100,000 fold, and 1,000,000 fold. 0.1 ml of the diluted liquids were dropped onto the Middlebrook 7H10 (Difco) solid medium. The resultant medium was cultured at 37° C. for 3 weeks. Then, the number of colony-forming units (CFU) was counted to determine the viable cell count in the *Mycobacterium tuberculosis* liquid.

For preparation of mouse macrophages, the mouse femur was severed and then both ends thereof were cut. A 1-ml syringe was filled with the RPMI-1640 medium (Gibco), which was then used to isolate and take marrow cells in the femur. Blood cells were removed from the taken marrow cells by a low-osmotic buffer, and then the number of marrow cells was measured using a microscope. After appropriate dilution with the RPMI-1640 medium, the marrow cells were seeded in a 96-well microplate at 100,000 cells per well. After culturing in a $CO_2$ incubator at 37° C. for 2 hours, cells other than the marrow cells were removed through exchange with a new RPMI-1640 medium. The medium was substituted with a culture supernatant of L929 cells, followed by culturing for 3 days. Again, the medium was substituted with a new culture supernatant of L929 cells, followed by culturing for 3 days.

In addition, as for infection with *Mycobacterium tuberculosis*, the frozen *Mycobacterium tuberculosis* was thawed, and then diluted with the RPMI-1630 medium to contain 1,000,000 viable cells per 0.2 ml of medium. The dilution liquid of *Mycobacterium tuberculosis* was filtered with a 5 µM syringe filter, and then the *Mycobacterium tuberculosis* was dispensed in the prepared macrophage culture wells such that the *Mycobacterium tuberculosis* count was ten times the macrophages count. The culturing was performed at 37° C. for 4 hours, followed by washing three times with the RPMI-640 medium and then dispensing of a new RPMI-1630 medium.

Then, the compounds of Chemical Formulas 1 to 4 were diluted with the RPMI-1640 medium by two-fold serial dilution, and then applied to respective wells to final concentrations of 100 µM, 50 µM, 25 µM, 12.5 µM, 6.25 µM, 3.125 µM, and 1.56 µM. Here, one group consisted of three wells. After application of the compounds, the culturing was performed in a $CO_2$ incubator at 37° C. for 7 days. In addition, the cultured cells were washed three times with the RPMI-1640 medium, followed by an exchange with the RPMI-1640 medium containing 0.1% saponin (Sigma-Aldrich). After culturing for 10 minutes, the supernatant was removed. The *Mycobacterium tuberculosis* remaining in each well was appropriately diluted by ten-fold series dilution, and then seeded on the Middlebrook 7H10 (Difco) solid medium, followed by culturing for 3 weeks. The number of CFU of *Mycobacterium tuberculosis* was counted to determine the viable cell count of *Mycobacterium tuberculosis*. The results were shown in FIGS. 13a to 13c. Meanwhile, moxifloxacin (Bayer AG) and rifampicin (3-{[(4-Methyl-1-Piperazinyl)imino]methyl}rigamycin) were used as control groups.

Figure 13A:
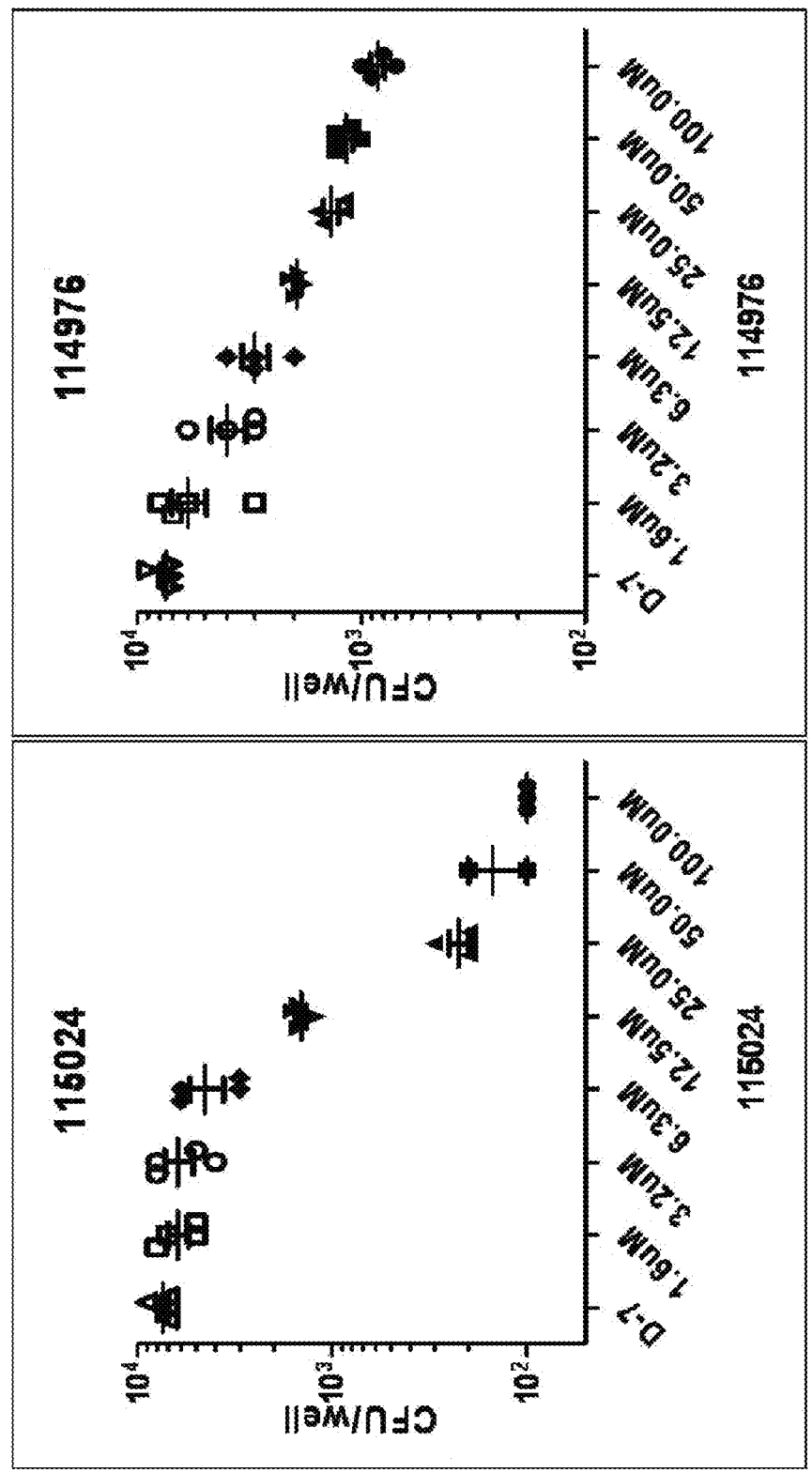
Figure 13C:
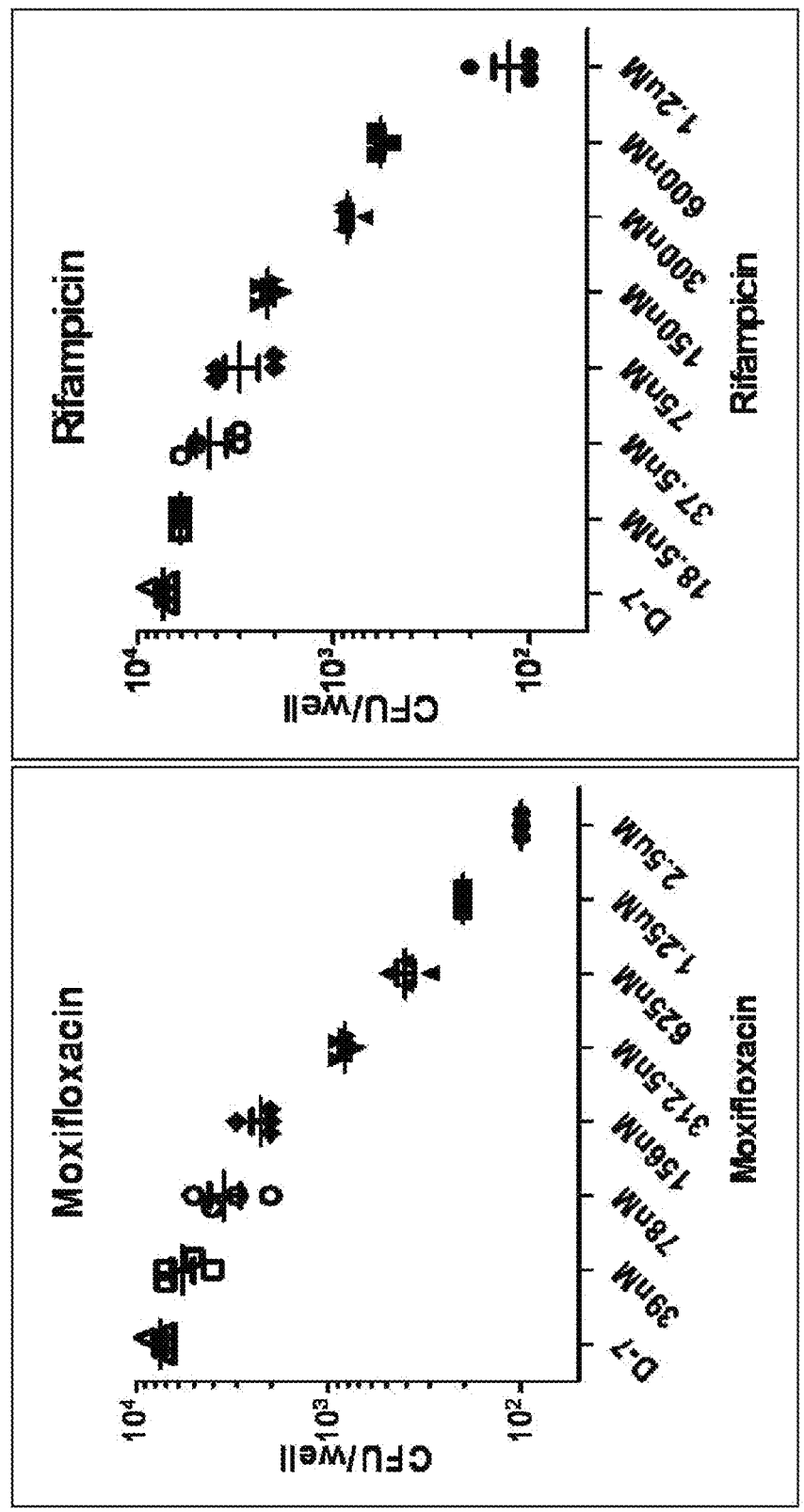

As can be seen from FIGS. 13a to 13c, the survival rate of Mycobacterium tuberculosis in the marrow cell-derived macrophages was reduced by the treatment with the compounds in a concentration-dependent manner.

Example 4

Cytotoxicity Test of Compounds

In order to find whether the compounds kill *Mycobacterium tuberculosis* by their own toxicity or specifically act on the target to inhibit the growth of *Mycobacterium tuberculosis*, the toxicity of the compounds was tested by treating *Mycobacterium tuberculosis* with the compounds alone using the CellTiter 96 Non-Radioactive Cell Proliferation Assay kit form Promega, USA.

Specifically, the Vero cell line under freezing storage (ATCC CCL-81) was thawed, and cultured in the DMEM medium (Gibco) for 4 days. The number of serially passaged cells was measured, and then the Vero cells were seeded in a 96-well microplate at 10,000 cells per well. The cells were cultured in the presence of 5% $CO_2$ at 37° C. overnight. Then, the compounds of Chemical Formulas 1 to 4 were diluted with the RPMI-1640 medium by two-fold serial dilution, and then applied to respective wells to final concentrations of 100 μM, 50 μM, 25 μM, 12.5 μM, 6.25 μM, 3.125 μM, and 1.56 μM. Here, one group consisted of three wells. After the compounds were applied, the cells were cultured in a $CO_2$ incubator at 37° C. for 3 days.

Cytotoxicity was measured according to the method of Promega Inc., and 15 μl of a staining solution was applied to each well of the 96-well plate. The cells were incubated in a $CO_2$ incubator at 37° C. for 4 hours, and then 100 μl of a quiescent solution was applied thereto. The absorbance of each well was measured at 570 nm using an absorbance measurement equipment from Molecular Devices. The absorbance values of wells not containing the compounds of Chemical Formulas 1 to 4 were compared with those of wells containing the compounds of Chemical Formulas 1 to 4 to determine the inhibition (%). The correlation between inhibition and concentration was calculated using the Prism software from Graphpad to determine $IC_{50}$ (concentration at 50% inhibition) value. The results for the Vero cell line and the marrow cell-derived macrophages were summarized in Table 2 below. The marrow cell-derived macrophages were prepared by the method as described in Example 3 above.

TABLE 2

|   | $IC_{50}$ (μM) (Vero cell line) | $IC_{50}$ (μM) (macrophages) |
|---|---|---|
| Chemical Formula 1 (115024) | 75.17 | >100 |
| Chemical Formula 2 (114976) | 36.41 | >100 |
| Chemical Formula 3 (114991) | 108.6 | >100 |
| Chemical Formula 4 (127999) | 157.5 | >100 |

The results for the *Mycobacterium* sp. strain JC1 wild type were summarized in Table 3 below.

TABLE 3

|   | Compound analog + JC 1 wild type (percentage (%) of CFU inhibition) | | |
|---|---|---|---|
| Concentration | 12.5 μM | 25 μM | 50 μM |
| Chemical Formula 1 (115024) | 0 | 2 | 6 |
| Chemical Formula 2 (114976) | 3 | 9 | 12 |
| Chemical Formula 3 (114991) | 4 | 2 | 8 |
| Chemical Formula 4 (127999) | 2 | 4 | 16 |

As can be determined from Tables 2 and 3 above, the compounds do not kill *Mycobacterium tuberculosis* by their own toxicity, but specifically act on the target CO-DH to inhibit the growth of *Mycobacterium tuberculosis*.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating tuberculosis, the method comprising:
administering to a subject a pharmaceutical composition containing: (a) a pharmaceutically effective amount of a compound represented by Formula 1 and (b) a pharmaceutically acceptable carrier:

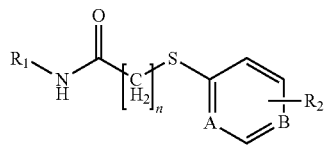

[Formula 1]

wherein, $R_1$ is

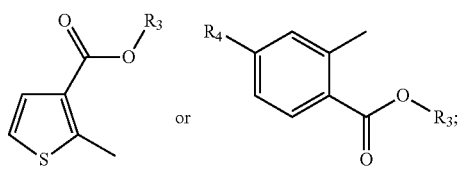

$R_3$ is H or $C_1$-$C_{10}$ alkyl;

$R_4$ is H, hydroxyl, halogen, $C_1$-$C_{10}$ alkyl, or $C_3$-$C_{15}$ cycloalkyl;

$R_2$ is H, hydroxyl, halogen, $C_1$-$C_{10}$ alkyl, $C_3$-$C_{15}$ cycloalkyl, $C_2$-$C_{10}$ alkenyl, or $C_1$-$C_8$ alkoxy;

A and B each are independently CH or N; and n is a integer of 1 to 5.

2. The method of claim 1, wherein the compound represented by Formula 1 is a compound represented by Formula 2:

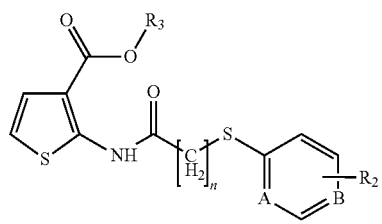

[Formula 2]

wherein $R_2$ is H, hydroxyl, halogen, or $C_1$-$C_{10}$ alkyl;

A and B each are independently CH or N;

n is an integer of 1 to 3; and $R_3$ is H or $C_1$-$C_{10}$ alkyl.

3. The method of claim 1, wherein the compound represented by Formula 1 is a compound represented by Formula 3 below:

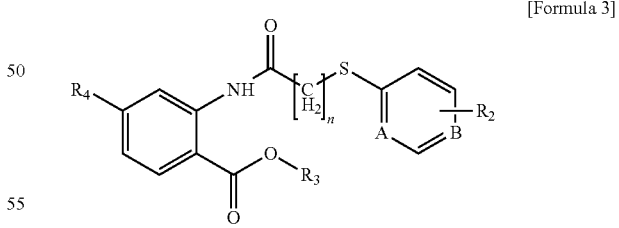

[Formula 3]

wherein $R_2$ is H, hydroxyl, halogen, or $C_1$-$C_{10}$ alkyl;

A and B each are independently CH or N;

n is an integer of 1 to 3;

$R_3$ is H or $C_1$-$C_{10}$ alkyl; and $R_4$ is H, hydroxyl, halogen, or $C_1$-$C_{10}$ alkyl.

4. The method of claim 2, wherein the compound represented by Formula 2 is a compound represented by Formula 4:

[Formula 4]

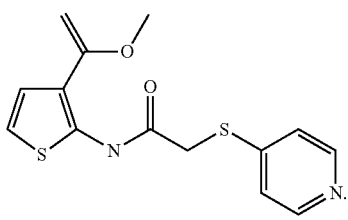

5. The method of claim 3, wherein the compound represented by Formula 3 is a compound selected from the group consisting of Formulas 5 to 7:

[Formula 5]

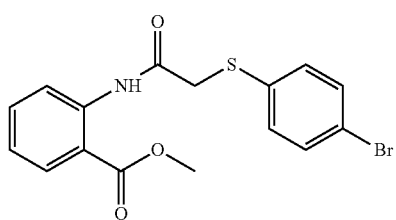

[Formula 6]

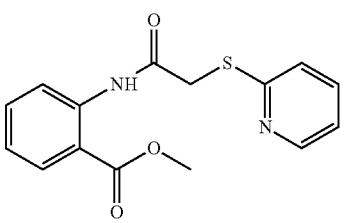

[Formula 7]

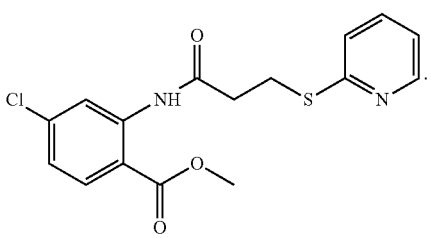

6. The method of claim 1, wherein the compound inhibits the transcription of carbon monoxide dehydrogenase (CO-DH) genes.

7. The method of claim 1, wherein the compound inhibits the expression of CO-DH genes.

8. The method of claim 1, wherein the tuberculosis is eye tuberculosis, skin tuberculosis, adrenal tuberculosis, renal tuberculosis, epididymal tuberculosis, lymphatic gland tuberculosis, laryngeal tuberculosis, middle ear tuberculosis, intestinal tuberculosis, multidrug-resistant tuberculosis, pulmonary tuberculosis, sputum tuberculosis, bone tuberculosis, throat tuberculosis, lymphatic tuberculosis, lung deficiency, breast tuberculosis, or spinal tuberculosis.

* * * * *

SEQUENCE LISTING

<160> NUMBER OF SEQ ID NOS: 7

<210> SEQ ID NO 1

<400> SEQUENCE: 1

000

<210> SEQ ID NO 2
<211> LENGTH: 21
<212> TYPE: DNA
<213> ORGANISM: Artificial Sequence
<220> FEATURE:
<223> OTHER INFORMATION: cutA-rev

<400> SEQUENCE: 2
cagatcggcg gggtcgctct g                    21

<210> SEQ ID NO 3
<211> LENGTH: 20
<212> TYPE: DNA
<213> ORGANISM: Artificial Sequence

```
<220> FEATURE:
<223> OTHER INFORMATION: cutR-for

<400> SEQUENCE: 3
gagccccgac gacgttcggg                                                  20

<210> SEQ ID NO 4
<211> LENGTH: 20
<212> TYPE: DNA
<213> ORGANISM: Artificial Sequence
<220> FEATURE:
<223> OTHER INFORMATION: orf1-for

<400> SEQUENCE: 4
ggcgtgggta tggaggtctt                                                  20

<210> SEQ ID NO 5
<211> LENGTH: 20
<212> TYPE: DNA
<213> ORGANISM: Artificial Sequence
<220> FEATURE:
<223> OTHER INFORMATION: orf2-rev

<400> SEQUENCE: 5
gtcactcgtg accgcagcat                                                  20

<210> SEQ ID NO 6
<211> LENGTH: 797
<212> TYPE: PRT
<213> ORGANISM: Mycobacterium sp. JC1

<400> SEQUENCE: 6
```

Met Thr Thr Ala Asp Val Ile Glu Asp Asn Glu Thr Ala Asp Asn Asp
1               5                   10                  15

Lys Lys Pro Cys Cys Tyr Gly Arg Met Leu Arg Lys Glu Asp Pro Arg
            20                  25                  30

Phe Ile Arg Gly Arg Gly Asn Tyr Val Asp Asp Val Gln Leu Pro Gly
        35                  40                  45

Met Leu His Leu Ala Ile Leu Arg Ser Pro Phe Ala His Ala Asn Ile
    50                  55                  60

Val Ser Val Asp Ile Ser Ala Ala Gln Ala His Pro Lys Val Lys Leu
65                  70                  75                  80

Val Val Thr Gly Ala Met Leu Ala Glu Lys Gly Leu Ala Val Met Pro
                85                  90                  95

Thr Leu Ser Asn Asp Val Gln Ala Val Leu Ala Thr Asp Arg Val Arg
            100                 105                 110

Phe Gln Gly Gln Glu Val Ala Phe Val Val Ala Glu Asp Arg Tyr Ser
        115                 120                 125

Ala Arg Asp Ala Leu Glu Leu Ile Asp Val Glu Tyr Glu Ala Leu Asp
    130                 135                 140

Pro Val Ile Asp Val Arg Lys Ala Leu Asp Pro Gly Ala Glu Val Ile
145                 150                 155                 160

Arg Thr Asp Leu Glu Gly Lys Thr Asp Asn His Cys Phe Asp Val Glu
                165                 170                 175

Thr Gly Asp Ala Ala Ala Thr Asp Ala Ala Phe Ala Lys Ala Asp Val
            180                 185                 190

Val Val Thr Gln Glu Ile Ile Tyr Pro Arg Val His Pro Cys Pro Met
        195                 200                 205

Glu Thr Cys Gly Ala Val Ala Asp Leu Asp Pro Val Ser Gly Lys Leu

```
              210                 215                 220
Arg Leu Val Ser Thr Thr Gln Ala Pro His Ala His Arg Thr Leu Tyr
225                 230                 235                 240

Ala Leu Val Ala Gly Leu Pro Glu His Lys Ile Gln Val Ile Ser Pro
                245                 250                 255

Asp Ile Gly Gly Gly Phe Gly Asn Lys Val Pro Ile Tyr Pro Gly Tyr
                260                 265                 270

Val Cys Ala Ile Val Gly Ser Leu Leu Gly Lys Pro Val Lys Trp
                275                 280                 285

Met Glu Asp Arg Ala Glu His Leu Met Ser Thr Gly Phe Ala Arg Asp
            290                 295                 300

Tyr Val Met Leu Gly Glu Ile Ala Ala Thr Lys Asp Gly Lys Ile Leu
305                 310                 315                 320

Ala Ile Arg Ser Asn Val Leu Ala Asp His Gly Ala Phe Asn Gly Thr
                325                 330                 335

Ala Ala Pro Val Lys Tyr Pro Ala Gly Phe Phe Gly Val Phe Thr Gly
                340                 345                 350

Ser Tyr Asp Ile Glu Ala Ala Tyr Cys His Met Thr Ala Val Tyr Thr
            355                 360                 365

Asn Lys Ala Pro Gly Gly Val Ala Tyr Ala Cys Ser Phe Arg Ile Thr
370                 375                 380

Glu Ala Val Tyr Phe Val Glu Arg Leu Val Asp Cys Leu Ala Phe Asp
385                 390                 395                 400

Leu Arg Met Asp Pro Val Glu Leu Arg Leu Arg Asn Leu Leu Lys Pro
                405                 410                 415

Glu Gln Phe Pro Tyr Lys Ser Lys Thr Gly Val Val Tyr Asp Ser Gly
                420                 425                 430

Asp Tyr Glu Lys Thr Leu Arg Leu Ala Met Asp Met Ile Gly Tyr Asp
            435                 440                 445

Gly Leu Arg Lys Glu Gln Ala Glu Lys Arg Ala Arg Gly Glu Leu Met
450                 455                 460

Gly Ile Gly Val Ser Phe Phe Thr Glu Ala Val Gly Ala Gly Pro Arg
465                 470                 475                 480

Lys Asp Met Asp Ile Leu Gly Leu Gly Met Ala Asp Gly Cys Glu Leu
                485                 490                 495

Arg Val His Pro Thr Gly Lys Ala Val Val Arg Leu Ser Val Gln Thr
                500                 505                 510

Gln Gly Gln Gly His Glu Thr Thr Phe Ala Gln Ile Val Ala Glu Glu
            515                 520                 525

Leu Gly Ile Pro Pro Glu Asp Ile Asp Val His Gly Asp Thr Asp
530                 535                 540

Gln Thr Pro Phe Gly Leu Gly Thr Tyr Gly Ser Arg Ser Thr Pro Val
545                 550                 555                 560

Ser Gly Ala Ala Ala Ala Leu Val Ala Arg Lys Val Arg Asp Lys Ala
                565                 570                 575

Lys Ile Ile Ala Ser Gly Met Leu Glu Ala Ser Val Ala Asp Leu Glu
                580                 585                 590

Val Glu Lys Gly Ser Phe Arg Val Lys Gly Asp Pro Ala Ala Ser Val
            595                 600                 605

Thr Ile Gln Asp Ile Ala Met Arg Ala His Gly Ala Ala Asp Leu Pro
610                 615                 620

Glu Gly Leu Glu Gly Gly Leu Asp Ala Gln Val Cys Tyr Asn Pro Glu
                630                 635                 640
```

```
Asn Met Thr Tyr Pro Tyr Gly Ala Tyr Phe Cys Val Val Asp Val Asp
                645             650                 655

Pro Gly Thr Ala Gln Val Lys Val Arg Arg Phe Leu Ala Val Asp Asp
                660             665                 670

Cys Gly Thr Arg Ile Asn Pro Met Ile Ile Glu Gly Gln Val His Gly
                675             680                 685

Gly Ile Val Asp Gly Ile Gly Met Ala Leu Met Glu Met Ile Ala Phe
                690             695                 700

Asp Glu Gln Gly Asn Cys Leu Gly Gly Ser Leu Met Asp Tyr Leu Ile
705                 710             715                 720

Pro Thr Ala Met Glu Val Pro His Phe Glu Thr Gly His Thr Val Thr
                725             730                 735

Pro Ser Pro His His Pro Ile Gly Ala Lys Gly Val Gly Glu Ser Ala
                740             745                 750

Thr Val Gly Ser Pro Pro Ala Val Val Asn Ala Val Val Asp Ala Leu
                755             760                 765

Ala Pro Phe Gly Val Arg His Ala Asp Met Pro Leu Asn Pro Ser Arg
                770             775             780

Val Val Glu Ala Met Gln Gly Arg Ala Thr Pro Pro Ile
785                 790             795

<210> SEQ ID NO 7
<211> LENGTH: 330
<212> TYPE: PRT
<213> ORGANISM: Artificial Sequence
<220> FEATURE:
<223> OTHER INFORMATION: CutA with a deletion of Mycobacterium sp.
      strain JC1 cutA- mutant

<400> SEQUENCE: 7

Met Thr Thr Ala Asp Val Ile Glu Asp Asn Glu Thr Ala Asp Asn Asp
1               5                   10                  15

Lys Lys Pro Cys Cys Tyr Gly Arg Met Leu Arg Lys Glu Asp Pro Arg
                20                  25                  30

Phe Ile Arg Gly Arg Gly Asn Tyr Val Asp Asp Val Gln Leu Pro Gly
                35                  40                  45

Met Leu His Leu Ala Ile Leu Arg Ser Pro Phe Ala His Ala Asn Ile
                50                  55                  60

Val Ser Val Asp Ile Asp Val His Gly Asp Thr Asp Gln Thr Pro
65                  70                  75                  80

Phe Gly Leu Gly Thr Tyr Gly Ser Arg Ser Thr Pro Val Ser Gly Ala
                85                  90                  95

Ala Ala Leu Val Ala Arg Lys Val Arg Asp Lys Ala Lys Ile Ile
                100                 105                 110

Ala Ser Gly Met Leu Glu Ala Ser Val Ala Asp Leu Glu Val Glu Lys
                115                 120                 125

Gly Ser Phe Arg Val Lys Gly Asp Pro Ala Ala Ser Val Thr Ile Gln
                130                 135                 140

Asp Ile Ala Met Arg Ala His Gly Ala Ala Asp Leu Pro Glu Gly Leu
145                 150                 155                 160

Glu Gly Gly Leu Asp Ala Gln Val Cys Tyr Asn Pro Glu Asn Met Thr
                165                 170                 175

Tyr Pro Tyr Gly Ala Tyr Phe Cys Val Val Asp Val Asp Pro Gly Thr
                180                 185                 190

Ala Gln Val Lys Val Arg Arg Phe Leu Ala Val Asp Asp Cys Gly Thr
```

-continued

```
            195                 200                 205
Arg Ile Asn Pro Met Ile Ile Glu Gly Gln Val His Gly Gly Ile Val
        210                 215                 220

Asp Gly Ile Gly Met Ala Leu Met Glu Met Ile Ala Phe Asp Glu Gln
225                 230                 235                 240

Gly Asn Cys Leu Gly Gly Ser Leu Met Asp Tyr Leu Ile Pro Thr Ala
                245                 250                 255

Met Glu Val Pro His Phe Glu Thr Gly His Thr Val Thr Pro Ser Pro
            260                 265                 270

His His Pro Ile Gly Ala Lys Gly Val Gly Glu Ser Ala Thr Val Gly
        275                 280                 285

Ser Pro Pro Ala Val Val Asn Ala Val Val Asp Ala Leu Ala Pro Phe
    290                 295                 300

Gly Val Arg His Ala Asp Met Pro Leu Asn Pro Ser Arg Val Val Glu
305                 310                 315                 320

Ala Met Gln Gly Arg Ala Thr Pro Pro Ile
                325                 330
```